(12) United States Patent
Carver

(10) Patent No.: US 11,878,012 B2
(45) Date of Patent: Jan. 23, 2024

(54) COMPOSITIONS AND METHODS FOR TREATING TRAUMATIC BRAIN INJURY

(71) Applicant: Board of Regents, the University of Texas System, Austin, TX (US)

(72) Inventor: Chase Carver, San Antonio, TX (US)

(73) Assignee: Board of Regents, The University of Texas System, Austin, TX (US)

(*) Notice: Subject to any disclaimer, the term of this patent is extended or adjusted under 35 U.S.C. 154(b) by 185 days.

(21) Appl. No.: 17/185,031

(22) Filed: Feb. 25, 2021

(65) Prior Publication Data
US 2022/0125779 A1    Apr. 28, 2022

Related U.S. Application Data

(60) Provisional application No. 62/981,839, filed on Feb. 26, 2020.

(51) Int. Cl.
*A61K 31/4709*    (2006.01)
*A61P 25/28*    (2006.01)
*A61K 45/06*    (2006.01)
*A61K 31/4184*    (2006.01)

(52) U.S. Cl.
CPC ...... *A61K 31/4709* (2013.01); *A61K 31/4184* (2013.01); *A61K 45/06* (2013.01); *A61P 25/28* (2018.01)

(58) Field of Classification Search
CPC .................................................. A61K 31/4709
See application file for complete search history.

(56) References Cited

U.S. PATENT DOCUMENTS 10,246,439 B2 * 4/2019 Granger ............. C07D 487/08
2014/0179750 A1 * 6/2014 Jiang .................. A61P 35/00
548/503

OTHER PUBLICATIONS

Akbulut et al. (2015) Angew Chem Int Ed Engl 54:3787-3791.
Becker et al. (2008) J Neurosci 28:13341-13353.
Broker-Lai et al. (2017) EMBO J 36:2770-2789.
Carver et al. (2014) J Neurosci 34:14181-14197.
Chung et al. (2006a) Proc Natl Acad Sci U S A 103:8870-8875.
Cohen et al. (2007) Prog Brain Res 161:143-169.
Dengler et al. (2017) Sci Rep 7:42090.
Fowler et al. (2007) PLoS One 2:e573.
He et al. (2012) J Neurosci 32:9383-9395.
Hernandez et al. (2008a) J Gen Physiol 132:361-381.
Hernandez et al. (2008b) J Physiol 586:1811-1821.
Hernandez et al. (2009) J Gen Physiol 134:437-448.
Hester and Danzer (2013) J Neurosci 33:8926-8936.
Homayoun et al. (2000) Neurochem Res 25:269-275.
Jiang et al. (1994) Brain Res 651:123-128.
Ko and Kang (2017) Neuropharmacology 121:120-129.
Krook-Magnuson et al. (2015) J Physiol 593:2379-2388.
Lyeth et al. (1996) Brain Res 742:63-70.
Madroñal et al. (2016) Nat Commun 7:10923.
Michel et al. (2005) Neuropharmacology 48:796-809.
Miller et al. (2011) J Biol Chem 286:33436-33446.
Mori et al. (2015) Front Pharmacol 6:22.
Owsianik et al. (2006) Annu Rev Physiol 68:685-717.
Phelan et al. (2012) Mol Pharmacol 81:384-392.
Ramsey et al. (2006) Annu Rev Physiol 68:619-647.
Reddy and Kuruba (2013) Int J Mol Sci 14:18284-18318.
Rubaiy et al. (2017) J Biol Chem 292:8158-8173.
Santhakumar et al. (2005) J Neurophysiol 93:437-453.
Scharfman and Myers (2016) Neurobiol Learn Mem 129:69-82.
Smith et al. (2012) J Vis Exp 69:4411.
Storch et al. (2012) J Biol Chem 287:3530-3540.
Strübing et al. (2001) Neuron 29:645-655.
Tai et al. (2011) Hippocampus 21:958-967.
Wu et al. (2010) Pharm Rev 62:381-404.
Yang et al. (2015) PLoS One 10:e0136255.
Zeng et al. (2015) Mol Neurobiol 52:562-572.
Zheng (2017) Adv Exp Med Biol 976:123-135.
Zheng and Phelan (2014) Cells 3:288-303.
Zhu et al. (2015) Br J Pharmacol 172:3495-3509.
Zimmerman et al. (2008) Eur J Neurosci 27:965-975.
Eslami et al., Neurol Res. Mar. 2016; 38(3):269-74.
Carver and Shapiro (2019) The Journal of Neuroscience 39(9):1566-1587.

* cited by examiner

*Primary Examiner* — Paul V Ward

(57) ABSTRACT

Certain embodiments are directed to methods and compositions for treating or preventing seizures in a subject using a therapeutic agent comprising one or more Transient Receptor Potential-Canonical 4/5 channel antagonists sufficient to regulate excitability of neurons in the brain of a subject.

9 Claims, 16 Drawing Sheets

Specification includes a Sequence Listing.

COMPOSITIONS AND METHODS FOR TREATING TRAUMATIC BRAIN INJURY

PRIORITY

This application claims priority to U.S. Provisional Patent Ser. No. 62/981,839 filed Feb. 26, 2020, which is incorporated herein by reference in its entirety.

STATEMENT REGARDING FEDERALLY FUNDED RESEARCH

This invention was made with government support under R01 NS094461, R01 NS043394, and T32 HL007446 awarded by the National Institutes of Health; and W81XWH1910400 awarded by the United States Department of Defense. The government has certain rights in the invention.

TECHNICAL FIELD

The present invention relates generally to the fields of cell and molecular biology, neurobiology, and treatment of traumatic brain injury, seizures, and epilepsy. In particular, the invention concerns the use of inhibitors of non-selective cation channels that promote excitability within neurons in the brain to treat traumatic brain injury, or treat epileptogenesis or seizure activity.

BACKGROUND

There are 150,000 newly diagnosed cases of epilepsy each year, and a total of over 3 million people in the United States with epilepsy. Traumatic brain injury (TBI) accounts for 20% of symptomatic epilepsies and 5-6% of all epilepsy (Garga and Lowenstein, 2006). The risk of post-traumatic epilepsy (PTE) is elevated for up to 10 years after a TBI event, but the highly indeterminate "latent period" can last between months and years without presentation of overt seizures (Frey, 2003; Lowenstein, 2009; Christensen et al., 2009). However, before seizure symptoms begin, TBI patients still experience pathophysiological changes in the brain that contribute to seizure susceptibility and gradual epileptogenesis. There are currently no FDA approved treatments for victims of TBI, nor are there any approved ways to successfully prevent epileptogenesis.

After the initial TBI, there is a secondary cascade of molecular changes in the brain that result in edema, neuronal damage, inflammation, and blood-brain barrier dysfunction (Pottker et al., 2017). Major contributing factors to TBI-induced changes are the deleterious, increased hyperexcitability and excitotoxicity of neurons that can lead to seizures. The hippocampus is a limbic structure that heavily relies on ion channel plasticity that is key for learning and memory, but maladaptive changes after TBI are linked to cognitive dysfunction, neurodegenerative disorders, and temporal lobe epilepsy (Cohen et al., 2007; Smith et al., 2012). Even though the site of injury may be confined to the cerebral cortex, the hippocampus still undergoes robust neuronal plasticity that has a pathophysiological role in hyperexcitability. In PTE models, selective neuronal death occurs in the hippocampus 1 to 7 days after injury, due to the cascade of hyperexcitability emanating throughout the brain (Golarai et al., 2001). Due to its important role in mediating seizure susceptibility, the hippocampus could serve as a critical brain structure in preventing posttraumatic seizures (PTS) from spreading from region to region.

Pleiotropic signaling systems in the hippocampus and perhaps elsewhere in the brain, in which input/output coupling of neuron circuitry is crucial to cerebral function and to halting adverse spread of hyperexcitability, among other events, promotes seizures. Overall, recent therapeutic strategies to prevent epileptogenesis after TBI, which can serve as a model of hyperexcitability in the targeting of TRPC channel blockade for the prevention of seizures, have not yielded improved outcomes, suggesting the urgent necessity of novel targets, including a greater depth of understanding behind the mechanisms of epileptogenesis. There remains a need for identification of novel molecular mechanisms and targets of acquired epileptogenesis that develop from TBI to achieve highly potent and efficacious control of neuronal activity to prevent epileptogenesis or anti-seizure activity. TRPC channel-driven neuromodulation can also be investigated for its contribution to PTS.

SUMMARY

Despite playing a strong role in brain hyperexcitability, TRPCs have not been explored as a target of treatment of either preventing epileptogenesis or anti-seizure activity. TRPC channels are non-selective cation channels that promote excitability within neurons in the brain. Certain aspects of the invention are directed to establishing therapeutics targeting TRPCs to prevent epileptogenesis or anti-seizure activity. A further aspect relates to use of therapeutics targeting TRPCs as basic science research tools to determine mechanisms of epileptogenesis in the brain.

A solution to address role of TRPC channels in epileptogenesis or anti-seizure activity has been discovered and is described herein. The solution resides in TRPC channel blockade in the hippocampus to prevent $G_q$-coupled activation of TRPC-mediated $Ca^{2+}$ influx, which inhibits neuronal excitation. In certain aspects systemic administration of the TRPC4/5 antagonist, e.g., M084 hydrochloride, can block the activity of chemoconvulsant-induced hyperexcitability of the muscarinic agonist pilocarpine, effectively preventing convulsant seizures.

1. Certain embodiments are directed to methods of treating seizures in a subject comprising administering to a subject having or at risk of seizure a Transient Receptor Potential-Canonical (TRPC) 4/5 channel antagonist. In certain aspects, the subject has experienced trauma to the brain or has experienced traumatic brain injury. Certain aspects are directed to methods of treating a subject that has experienced a traumatic brain injury comprising administering to a subject having experienced a TBI a Transient Receptor Potential-Canonical (TRPC) 4/5 channel antagonist. In certain aspects the TRPC 4/5 antagonist is administered 1, 2, 3, 4, 5, 6, 7, 8, 9, 10, 11, 12 days or weeks (including all values and ranges there between) after the TBI. Traumatic brain injury (TBI) is a nondegenerative, noncongenital insult to the brain from an external mechanical force, possibly leading to permanent or temporary impairment of cognitive, physical, and psychosocial functions, with an associated diminished or altered state of consciousness. Seizures can be caused by or be a result of traumatic brain injury (TBI) or head trauma. In other aspects, the TRPC4/5 channel antagonist selectively inhibits the formation, activation, or activity of TRPC4/5 channels. In certain aspects, the TRPC4/5 channel antagonist inhibits the formation, activation, or activity of TRPC4/5 channels and one or more other TRPC channels. The TRPC4/5 inhibitor can be a small molecule, protein, or nucleic acid molecule. In certain aspects, the TRPC4/5 channel antagonist is a benzimidazole or 2-aminobenzimidazole derivative, a 2-aminoquinoline derivative, or a combination thereof. In a particular aspect, the TRPC4/5 channel antagonist is M084 (n-butyl-1h-benzimidazol-2-amine) hydrochloride or ML204 (CAS No. 5465-86-1). In certain aspects, the TRPC4/5 channel antagonist is administered to the subject by a route selected from among a parenteral, intravenous, intraarterial, intramuscular, intracranial, nasal, or intraventricular route. The methods can further comprise or include administering one or more additional therapeutic agents to the subject. The one or more additional therapeutic agent can be a neuroprotective agent, an anticonvulsant agent, an antiepileptic agent, or a combination thereof. In certain aspects, the TRPC4/5 channel antagonist is administered to the subject before, at the same time, or after the additional therapeutic agent is administered to the subject. The administration of a TRPC4/5 channel antagonist can regulate/modulate the hyperexcitability of neurons in the hippocampus of the subject. In certain aspects the neurons are dentate gyms granule cells. In certain embodiments, the subject is a human subject.

Certain embodiments are directed to methods of regulating excitability of neurons in a subject, comprising administering a TRPC4/5 channel antagonist to the subject. In certain aspects, the subject is experiencing or has experienced an event that results in the subject having or at risk of having a seizure. The event can be a traumatic brain injury (TBI) or head trauma. In certain aspects, the neurons are in the hippocampus of the subject. In certain aspects, the neurons are dentate gyms granule cells. The TRPC4/5 channel antagonist can selectively inhibit the formation, activation, or activity of TRPC4/5 channels. The TRPC4/5 channel antagonist can inhibit the formation, activation or activity of TRPC4/5 channels and one or more other TRPC channels. The TRPC4/5 inhibitor can be a small molecule, protein, or nucleic acid molecule. In certain aspects, TRPC4/5 channel antagonist is a benzimidazole or 2-aminobenzimidazole derivative, a 2-aminoquinoline derivative, or a combination thereof. The TRPC4/5 channel antagonist can be M084 hydrochloride or ML204. In certain aspects, the subject is a human subj ect.

Certain embodiments are directed to compositions comprising or methods of using compositions comprising a TRPC4/5 channel antagonist, capable of being used to regulate excitability of neurons or in treating seizures in a subject having or at risk of having a seizure. The composition(s) can be administered to the subject by a route selected from among a parenteral, intravenous, intraarterial, intramuscular, intracranial, nasal, or intraventricular route. The composition can further comprise one or more additional therapeutic agents. The one or more additional therapeutic agent can be a neuroprotective agent, an anticonvulsant agent, an antiepileptic agent, or a combination thereof In certain aspects, the composition(s) can be administered to the subject before, at the same time, or after the additional therapeutic agent is administered to the subject.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

(FIG. 1A) Calcium green-1 fluorescence before and after bath-application of 77-LH-28-1 (3 μm) alone or in the presence of edelfosine (10 μm), the TRPC channel blockers M084 and ML204 (10 μm), or with the $IP_3R$ blocker, xestospongin-C (10 μm), in the internal pipette solution. Images depict 16-color pseudocolor heat maps of fluorescence intensity. (FIG. 1B) Summarized changes in fluorescence intensity over 0-12 min after perfusion of slices with 77-LH-28-1. n=5-7 cells per group. *p<0.05 versus 77-LH-28-1+edelfosine; †p<0.05 versus 77-LH-28-1 alone. (FIG. 1C) Summarized evoked action potential frequencies before (filled squares) and after application of 77-LH-28-1 (open circles) in the presence of xestospongin C. (FIG. 1D) Summarized evoked action potential frequencies during TRPC blockade with M084 and ML204 before (filled circles) and after bath-application of 77-LH-28-1 (open triangles) *p<0.05 versus TRPC block, control. (FIG. 1E) Plotted are summarized membrane potential values (voltage floor) in the presence of the TRPC4/5 channel antagonist M084 (10 μm). There were no significant differences in any values between those obtained in control ACSF and during application of 77-LH-28-1 (3 μm). *p<0.05; n=8 cells. Action potential properties derived from current-clamp recordings in presence of TRPC block are listed in Table 1. (FIG. 1F) In vivo pretreatment with TRPC channel antagonists confers protection from pilocarpine-induced chemoconvulsant seizures. Plots summarize the Racine seizure stage progression of adult mice that were treated with vehicle or M084 (10 mg/kg) to block TRPC4/5 channels 30 min before challenge with pilocarpine (280 mg/kg). *p<0.05 versus vehicle control; n=8 mice per group.

(FIG. 2A) Summarized data for real-time PCR quantification of TRPC1, 4, and 5 mRNA of microdissected parietal cortex (CTX), dentate gyms (DG), hippocampal CA3, and hippocampal CA1 regions 7 days after sham control or TBI procedure. Within x axis, prefix of c denotes the hemisphere that is contralateral to injury and prefix of i denotes the hemisphere ipsilateral to injury. All mRNA samples are normalized to HPRT mRNA as control. There were significant increases in TRPC4 and TRPC5 mRNA in all brain regions of TBI mice compared to sham control mice littermates. * p<0.05 vs. contralateral TBI region. n=4 mice per group. (FIG. 2B-FIG. 2C) Summarized data for western blot quantification of TRPC4 (B, n=7-13 animals per group) and TRPC5 (C, n=5-7 animals per group) from microdissected brain regions in mice 7 days after TBI. Blots were normalized to β-actin protein as loading control. (FIG. 2D-FIG. 2E) Shown are summarized plots of mean percent difference in protein between ipsilateral and contralateral microdissected regions from data in D and E. For figures B-E: * p<0.05 vs. sham. All bars represent the mean ±S.E.M.

(FIG. 3A) Representative images of parietal cortex from sham and TBI TRAP mice that were administered 4-OHT at t=12 hours before procedure. Prefix "c" denotes contralateral, prefix "i" denotes ipsilateral. Red=Fos-tdTomato; blue=DAPI. (FIG. 3B) Representative images of hippocampal subregions from sham and TBI TRAP mice that were administered 4-OHT at t=12 hours before procedure. (FIG. 3) Summarized quantification of cFos+neurons in sham and TBI TRAP mice activated at the time of TBI, as in A and B. (FIG. 3D) Representative images taken from sham mice, TBI mice, and TBI mice also administered M084 (10 mg/kg) (TBI+M084) that were administered 4-OHT t=7 days after procedure. (FIG. 3E) Summarized quantification of cFos+ neurons in sham, TBI, and TBI+M084 mice 7 days after procedure, as in D. All bars represent the mean ±S.E.M. * p<0.05 vs. sham. #p<0.04 vs TBI cDG. †p<0.05 vs. TBI of same region.

(FIG. 4D) Summarized number of DGGCs that were active in showing at least 1 $Ca^{2+}$ influx event during 0.3 mM ACh. (FIG. 4E) Cumulative probability distribution of the peak amplitude of GCaMP6f fluorescence (ΔF/F) for each DGGC from control, cTBI, and iTBI slices. D-Insert: summarized mean data of peak fluorescence.

(FIG. 5A) Cumulative probability distribution of the peak amplitude of GCaMP6f fluorescence (ΔF/F) for each DGGC from iTBI slices during EA (1 μM) or EA+M084 (10 μM) application. (FIG. 5B) Cumulative probability distribution of the $Ca^{2+}$ influx duration (in seconds) for each DGGC from iTBI slices during EA or EA+M084 application. (FIG. 5C) Summarized mean of peak fluorescence from data as in A. (FIG. 5D) Summarized mean of $Ca^{2+}$ influx duration from data as in B. All data bars represent the mean ±S.E.M. * p<0.05 vs. EA alone, Scale bars: 20 μm, 40× magnification with aqueous-immersed objective.

(FIG. 6A) Pentylenetetrazol (PTZ) kindling after TBI design schematic in which daily 35 mg/kg PTZ challenge occurs 1 or 7 days after TBI (top) or concurrent M084 (10 mg/kg) 1 hour before PTZ challenge (bottom). End-point criteria for kindling of mice was behavioral evidence of tonic-clonic motor seizure exhibited through tonic hindlimb extension. (FIG. 6B) Rate of PTZ kindling initiated in sham mice, mice 1 day after TBI, and mice 7 days after TBI. Bars summarize the mean number of days required to elicit the motor behavioral activity. * p<0.05 vs. sham. n=6-8 mice per group. (FIG. 6C) Cumulative progression of mice achieving clonic seizures after daily PTZ challenge, as a percentage of total animals per group. TBI mice challenged after delaying 1 day and 7 days showed similar rates of kindling and exhibited accelerated seizure activity compared to sham mice. (FIG. 6D) Rate of PTZ kindling 7 days after sham or TBI compared to mice treated with M084 from paradigm shown in bottom panel of A. Bars summarize the mean number of days required to elicit the motor behavioral activity. M084 treatment significantly impeded the progression of seizures compared to untreated TBI animals. * p<0.05 vs. TBI untreated, †p<0.05 vs. TBI with M084. n=6-7 mice per group. (FIG. 6E) Kaplan-Meier plot for mice exhibiting forelimb clonus over time, from data shown in E. (FIG. 6F) Kaplan-Meier plot for mice exhibiting tonic hindlimb extension over time, from data shown in E. All bars represent the mean ±S.E.M.

DESCRIPTION

Figure 1A:
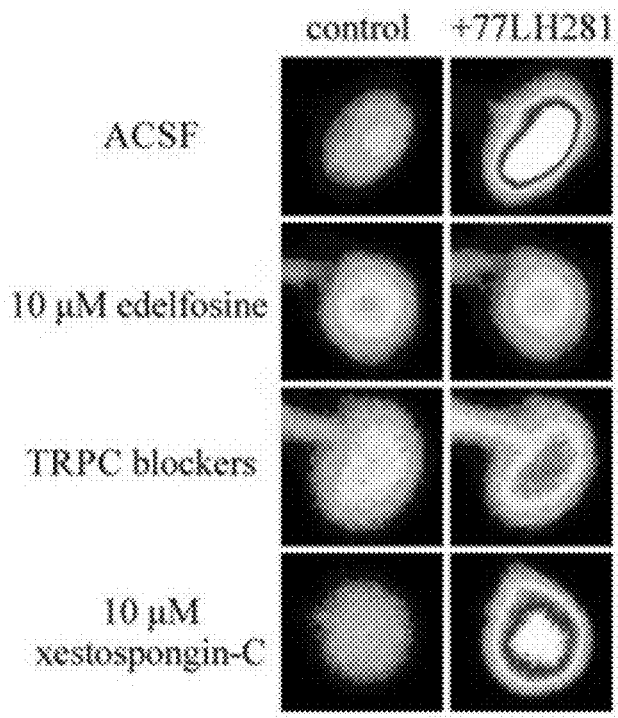
FIG. 1A-1F. Muscarinic stimulation of DGGCs induces intracellular rises in [$Ca^{2+}$] that is mostly due to TRPC4/5 channels, which underlie $M_1R$-induced hyperexcitability of DGGCs.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Canonical transient receptor potential (TRPC) channels are non-selective cation channels that are activated in response to phospholipase C (PLC) signaling, enabling $Ca^{2+}$ and Na+influx (PCa/PNa=TRPC1: nonselective, TRPC2-6: 1.1-9) and membrane depolarization, as well as $Ca^{2+}$-evoked second messenger cascades (Fowler et al., 2007; Owsianik et al., 2006; Storch et al., 2012; Mori et al., 2015). These channels are widely expressed in CNS neurons, and have been suggested to have a role in epilepsy and cell death after seizures (Zheng, 2017). Of the TRPC subtypes, TRPC4 and 5 comprise a majority of brain expression, with TRPC3, 1, and 6 moderately expressed, and TRPC2 and 7 demonstrating very low levels of expression (Fowler et al., 2007). TRCP1/4/5-containing heteromeric channels contribute to the modulation of neuronal excitability and synaptic transmission in the corticolimbic system, including learning and memory functions (Fowler et al., 2007; Broker-Lai et al., 2017).

The natural compound (-)-englerin A directly and potently activates TRPC4/5 channels (Akbulut et al., 2015). Whereas this compound has been primarily studied in cancer toxicity research, it has potential as a pharmacological tool to investigate endogenous TRPC channel physiology in the CNS. Furthermore, M084 (n-butyl-1h-benzimidazol-2-amine) is a TRPC4/5 inhibitor that crosses the blood-brain barrier and has been shown to have antidepressant and anxiolytic effects in mice (Yang et al., 2015). M084 has been studied as an anticonvulsant target of TRPC4/5 inhibition in the pilocarpine model of epilepsy. Recently, Pico145 was discovered as a highly selective inhibitor of TRPC1/4/5 channels with picomolar potency (Rubaiy et al., 2017). Therefore, recent advances in selective TPRC channel pharmacology can be used to precisely determine the mechanistic contribution of TRPC channels to neuronal pathophysiology.

$G_q$-coupled metabotropic receptors activate TRPC channel opening through phospholipase C intracellular signaling (Fowler et al., 2007). Pilocarpine is a nonselective muscarinic acetylcholine receptor (mAChR) agonist that is widely used as a chemoconvulsant for the induction of seizures and epileptogenesis in rodent models (Reddy and Kuruba, 2013). Muscarinic receptor-dependent depolarization, which induces synchronous neuronal firing and seizure, involves TRPC channel activation (Phelan et al., 2012). Pathophysiological modulation of mAChRs has been demonstrated to contribute to seizures in chronically epileptic rats (Zimmerman et al., 2008). High doses of pilocarpine induce a state of persistent seizures that do not terminate (status epilepticus), resulting in death, unless anticonvulsant intervention is achieved. Rodents which survive this period of status epilepticus subsequently experience spontaneous epileptic seizures. Previous data suggest that excessive activation of mAChR and PLC signal transduction after TBI contributes to long-term pathophysiology and neurological deficits (Jiang et al., 1994; Lyeth et al., 1996). Furthermore, sustained increase in diacylglycerol (DAG) production at the neuronal membrane after TBI suggests phospholipid-dependent initiation of downstream signaling pathways that contribute to the secondary injury cascade (Homayoun et al., 2000). Therefore, mAChR signaling and TRPC channels may be linked in their contribution to epileptogenesis after trauma.

TRPC knockout mouse models are less susceptible to pilocarpine-induced seizures and have reduced cell death resulting from excitotoxicity (Phelan et al., 2012; Zheng and Phelan, 2014, Ko and Kang, 2017). TRPC3 and TRPC6 exhibit increased expression in the temporal cortex of epilepsy patients as well as in the hippocampus of status epilepticus mice (Zeng et al., 2015). These studies suggest the involvement of TRPC channels in epileptogenesis, however, the contribution of TRPC channels in acquired epilepsies and PTE has not been previously explored. TRPC channels contribute to membrane depolarization (Fowler et al., 2007), but how these channels regulate intrinsic neuronal excitability in the cortex and hippocampus is not well studied. Previous studies have demonstrated that upregulation of voltage-gated T-type $Ca^{2+}$ channels contribute to epileptogenesis via increases to both $Ca^{2+}$ currents and neuronal burstfiring (Becker et al., 2008). Similar $Ca^{2+}$ influx through TRPC channels is suggested to contribute to hyperexcitability (Phelan et al., 2012).

Regulation of excitability and circuit behavior has been thoroughly studied in the hippocampus due to its fundamental role in temporal lobe epilepsy (Dengler et al., 2017; Poolos and Johnston, 2012; Takano and Coulter, 2012). The dentate gyms (DG) filters external, afferent inputs into the hippocampal circuit as a "gate-keeper" of excitability, crucial to the processing of physiological (Coulter and Carlson, 2007, Madroñal, et al., 2016) and pathophysilogical network functions (Krook-Magnuson et al., 2015). Since dentate gyms granule cells (DGGCs) are typically quiescent at rest, robust excitatory signaling at these neurons dramatically increases the activity of the hippocampus (Kobayashi and Buckmaster, 2003; Hester and Danzer, 2013; Scharfman and Myers, 2016). For electrical signals to propagate to downstream hippocampal processes, strong facilitation of DGGC firing is necessary (Henze et al., 2002). The fine-tuning of ion channel plasticity, axonal circuitry, and interneuron feedback contributes to the excitability of DGGCs as a key regulatory control over the hippocampus (Santhakumar et al., 2005). The strong innervation of DGGCs by cholinergic neurons originating in the medial septum/diagonal band of the basal forebrain suggests robust acetylcholine-driven neurotransmission. After TBI, the dentate gyms is diminished in its ability to regulate cortical input into the hippocampus, and this in turn results in increased CA3 network excitability disruptive dysfunction of hippocampal information processing (Folweiler et al., 2018). Preliminary studies have indicated that mAChR stimulation facilitates PLC-dependent activation of TRPC cation channels that contributes to aberrant hyperexcitability.

I. Definitions

As used herein, the term "epilepsy" refers to a disease characterized by an enduring predisposition to generate epileptic seizures and by the neurobiological, cognitive, psychological, and social consequences of this condition. Epilepsy has no identifiable cause in about half the people with the condition. In the other half, the condition may be traced to various factors, including: genetic influence; head trauma; brain conditions such as tumors or strokes; infectious diseases such as meningitis, AIDS and viral encephalitis; prenatal injury such as infection in the mother, poor nutrition or oxygen deficiencies; and developmental disorders such as autism and neurofibromatosis. Certain factors may increase the risk of epilepsy, including: age, with the onset of epilepsy is most common in children and older adults, though it can occur at any age; family history of epilepsy; head injuries; stroke and other vascular diseases; dementia; brain infections; and seizures in childhood resulting from high fevers, for example.

The term "epileptic seizure" refers to transient occurrence of signs and/or symptoms due to abnormal excessive or synchronous neuronal activity in the brain. Seizure symptoms can vary widely. Some people with epilepsy simply stare blankly for a few seconds during a seizure, while others repeatedly twitch their arms or legs. When seizures appear to result from abnormal activity in just one area of the brain, the seizures are classified as focal (partial) seizures. These seizures fall into two categories: focal seizures without loss of consciousness and focal seizures with impaired awareness. Focal seizures without loss of consciousness, once called simple partial seizures, do not cause a loss of consciousness. They may alter emotions or change the way things look, smell, feel, taste or sound. They may also result in involuntary jerking of a body part, such as an arm or leg, and spontaneous sensory symptoms such as tingling, dizziness and flashing lights. Focal seizures with impaired awareness, once called complex partial seizures, involve a change or loss of consciousness or awareness. During a complex partial seizure, a subject may stare into space and not respond normally to the environment or perform repetitive movements, such as hand rubbing, chewing, swallowing or walking in circles.

Seizures that appear to involve all areas of the brain are called generalized seizures. Six types of generalized seizures exist: absence seizures, tonic seizures, atonic seizures, clonic seizures, myoclonic seizures, and tonic-clonic seizures. Absence seizures, previously known as petit mal seizures, often occur in children and are characterized by staring into space or subtle body movements such as eye blinking or lip smacking. These seizures may occur in clusters and cause a brief loss of awareness. Tonic seizures cause stiffening of the muscles. These seizures usually affect muscles in the back, arms and legs and may cause you to fall to the ground. Atonic seizures, also known as drop seizures, cause a loss of muscle control, which may cause you to suddenly collapse or fall down. Clonic seizures are associated with repeated or rhythmic, jerking muscle movements. These seizures usually affect the neck, face and arms. Myoclonic seizures usually appear as sudden brief jerks or twitches of the arms and legs. Tonic-clonic seizures, previously known as grand mal seizures, are the most dramatic type of epileptic seizure and can cause an abrupt loss of consciousness, body stiffening and shaking, and sometimes loss of bladder control or biting the tongue.

As used herein, the term "TRPC" refers to a family of transient receptor potential cation channels in animals. TRPC channels form the subfamily of channels in humans most closely related to drosophila TRPC channels. Structurally, members of this family possess a number of similar characteristics, including 3 or 4 ankyrin repeats near the N-terminus and a TRPC box motif containing the invariant EWKFAR sequence at the proximal C-terminus. These channels are non-selectively permeable to cations, with a selectivity of calcium over sodium variable among the different members. Many of TRPC channel subunits are able to coassemble. The predominant TRPC channels in the mammalian brain are the TRPC 1, 4, and 5 and they are densely expressed in corticolimbic brain regions, like the hippocampus, prefrontal cortex and lateral septum. These 3 channels are activated by the metabotropic glutamate receptor 1 agonist dihydroxyphenylglycine. In general, TRPC channels can be activated by phospholipase C stimulation, with some members also activated by diacylglycerol. There is one at least one report that TRPC1 is also activated by stretching of the membrane and TRPC5 channels are activated by extracellular reduced thioredoxin. It has been proposed that TRPC channels underlie the calcium release activated channels observed in many cell types. These channels open due to the depletion of intracellular calcium stores. Two other proteins, stromal interaction molecules (STIMs) and Orais, however, have more recently been implicated in this process. STIM1 and TRPC1 can coassemble, complicating the understanding of this phenomenon.

As used herein, the term "TRPC channel" refers to a canonical transient receptor potential channel. TRPC channels are multimeric $Ca^{2+}$ permeable non-selective cation channels, and reference to a TRPC channel includes reference to both homomeric and heteromeric channels formed by one or more of the TRPC1, TRPC2, TRPC3, TRPC4, TRPC5, TRPC6 and TRPC7 polypeptides, including isoforms and splice variants thereof. Reference to a TRPC channel includes reference to human TRPC channels as well as non-human TRPC channels, including, but not limited to, mouse, rat, guinea pig, dog, horse, cat, sheep, monkey and chimpanzee TRPC channels. These channels are widely expressed in CNS neurons, and have been suggested to have a role in epilepsy and cell death after seizures. Of the TRPC subtypes, TRPC4 and 5 comprise a majority of brain expression, with TRPC3, 1, and 6 moderately expressed, and TRPC2 and 7 demonstrating very low levels of expression.

As used herein, the term "TRPC4" refers to a member of the transient receptor potential cation channels. TRPC4 forms a non-selective calcium-permeable cation channel that is activated by Gαi-coupled receptors, Gαq-coupled receptors and tyrosine kinases, and plays a role in multiple processes including endothelial permeability, vasodilation, neurotransmitter release and cell proliferation. TRPC4 has been shown to be present in high abundance in the corticolimbic regions of the brain. In addition, TRPC4 mRNA is present in midbrain dopaminergic neurons in the ventral tegmental area and the substantia nigra. Single nucleotide polymorphisms in the TRPC4 gene may be associated with generalized epilepsy. The amino acid sequence for human TRPC 4 can be found in UniProtKB database as entry Q9UBN4.

As used herein, the term "TRPC4 channel" refers to a $Ca^{2+}$ permeable non-selective cation channel formed by a TRPC4 polypeptide. A TRPC4 channel can be homomeric (i.e. formed only by TRPC4 polypeptides) or heteromeric (i.e. formed by at least one TRPC4 polypeptide and one or more different TRPC polypeptides, such as a TRPC1, TRPC2, TRPC3, TRPC5, TRPC6 or TRPC7 polypeptide). TRPC4 channels include human TRPC4 channels as well as non-human TRPC4 channels, such as mouse, rat, guinea pig, dog, horse, cat, sheep, monkey and chimpanzee TRPC4 channels, and can be formed by any TRPC4 polypeptide. TRPC4 polypeptides include polypeptides encoded by the full length transcript from a TRPC4 gene (TRPC4α) as well polypeptides encoded by alternatively spliced transcripts (e.g. TRPC4β, TRPC4δ, TRPC4γ, TRPC4ε, TRPC4ζ, or TRPC4η).

As used herein, the term "TRPC5" refers to one of the seven mammalian transient receptor potential canonical proteins. TRPC5 is a multi-pass membrane protein and is thought to form a receptor-activated non-selective calcium permeant cation channel. The protein is active alone or as a heteromultimeric assembly with TRPC1, TRPC3, and TRPC4. It also interacts with multiple proteins including calmodulin, CABP1, enkurin, $Na^+$-$H^+$ exchange regulatory factor (NHERF), interferon-induced GTP-binding protein (MX1), ring finger protein 24 (RNF24), and SEC14 domain and spectrin repeat-containing protein 1 (SESTD1). TRPC5 is thought to be operated by a phosphatidylinositol second messenger system activated by receptor tyrosine kinases or G-protein coupled receptors. TRPC5 has also been shown to be calcium-selective and may be activated by intracellular calcium store depletion. TRPC5 has previously been suggested to be predominantly expressed in the brain. The amino acid sequence for human TRPC5 can be found in the UniProtKB database as entry Q9UL62.

As used herein, the term "TRPC5 channel" refers to a $Ca^{2+}$ permeable non-selective cation channel formed by a TRPC5 polypeptide. A TRPC4 channel can be homomeric (i.e. formed only by TRPC5 polypeptides) or heteromeric (i.e. formed by at least one TRPC5 polypeptide and one or more different TRPC polypeptides, such as a TRPC1, TRPC2, TRPC3, TRPC4, TRPC6 or TRPC7 polypeptide). TRPC5 channels include human TRPC5 channels as well as non-human TRPC5 channels, such as mouse, rat, guinea pig, dog, horse, cat, sheep, monkey and chimpanzee TRPC5 channels, and can be formed by any TRPC5 polypeptide. TRPC5 polypeptides include polypeptides encoded by the full length transcript from a TRPC5 gene as well polypeptides encoded by alternatively spliced transcripts.

As used herein, a "TRPC4 inhibitor," "TRPC5 inhibitor," "TRPC4/5 inhibitor" or an "inhibitor of TRPC4/5" or grammatical variations thereof refers to an agent that inhibits the expression or activity of a TRPC4 or 5 (TRPC4/5) polypeptide or channel, including variants or isoforms thereof. A TRPC4/5 inhibitor can selectively inhibit TRPC4/5 polypeptides and/or TRPC4/5 channels, or can inhibit TRPC4/5 polypeptides and/or TRPC4/5 channels and also inhibit one or more other polypeptides and/or channels, such as one or more other TRPC polypeptides and/or channels. The inhibition may be to an extent (in magnitude and/or spatially), and/or for a time, sufficient to produce the desired effect. Inhibition may be prevention, retardation, reduction or otherwise hindrance of TRPC4/5 expression and/or activity. Such inhibition may be in magnitude and/or be temporal or spatial in nature. Inhibition of expression of TRPC4/5 can be assessed using methods well known in the art to measure transcription and/or protein production. Inhibition of the activity of TRPC4/5 can be assessed by, for example, determining the ability of TRPC4/5 polypeptides to form a channel and/or the ability of TRPC4/5 channels to facilitate cation flux. Methods to assess TRPC4/5 activity by assessing TRPC4/5 channel conductance are described herein and can be used to determine the level of inhibition of TRPC4/5 activity resulting from a TRPC4/5 inhibitor. The expression and/or activity of TRPC4/5 can be inhibited by an agent by at least or about 10%, 15%, 20%, 25%, 30%, 35%, 40%, 45%, 50%, 55%, 60%, 65%, 70%, 75%, 80%, 85%, 90%, 95% or more compared to the expression and/or activity of TRPC4/5 in the absence of the agent. A TRPC4/5 inhibitor may be specific or selective for TRPC4/5 or may be capable of inhibiting the expression or activity of one or more TRPC4/5 polypeptides or channels in addition to TRPC4/5. Furthermore, a TRPC4/5 inhibitor may act directly or indirectly on TRPC4/5. Accordingly the inhibitor may operate directly or indirectly on TRPC4/5 polypeptides or channels, a TRPC4/5 mRNA or gene, or alternatively act via the direct or indirect inhibition of any one or more components of a TRPC4/5-associated pathway. Such components may be molecules activated, inhibited or otherwise modulated prior to, in conjunction with, or as a consequence of TRPC4/5 polypeptide or channel activity.

As used herein, "TRPC4/5 activity" or an "activity of TRPC4/5" refers to any activity associated with TRPC4/5 polypeptides and/or TRPC4/5 channels, including, but not limited to, the ability of TRPC4/5 polypeptides to form a channel, the ability of TRPC4/5 channels to be activated, and the ability of TRPC4/5 channels to facilitate cation flux.

The term "inhibiting" and variations thereof such as "inhibition" and "inhibits" as used herein in relation to excitability of neurons, or the formation, activity or activation or formation of TRPC channels (e.g., TRPC, TRPC4, and TRPC5 channels, and variations thereof), means complete or partial inhibition of neuron excitability or complete or partial inhibition of the formation, activity or activation of TRPC channels. The inhibition may be to an extent (in magnitude and/or spatially), and/or for a time, sufficient to produce the desired effect. Inhibition may be prevention, retardation, reduction or otherwise hindrance of excitability of neurons or of the formation, activity or activation of TRPC channels. Such inhibition may be in magnitude and/or be temporal or spatial in nature. Inhibition of the neuron excitability by an agent (i.e. a TRPC4/5 inhibitor or antagonist) can be assessed by measuring excitability in the presence and absence of the agent following an event that would normally trigger excitability, such as, for example, oxygen deprivation. The excitability of neurons can be inhibited by the agent by at least or about 10%, 15%, 20%, 25%, 30%, 35%, 40%, 45%, 50%, 55%, 60%, 65%, 70%, 75%, 80%, 85%, 90%, 95% or more compared to the excitability of neurons that have not been exposed to the agent. Inhibition of the activation, activity or formation of TRPC channels by an agent (i.e. a TRPC4/5 inhibitor) can be assessed by measuring, for example, cation flux, membrane conductance, and/or $Ca^{2+}$ entry into cells in the presence and absence of the agent. The activation, activity or formation of TRPC channels can be inhibited by the agent by at least or about 10%, 15%, 20%, 25%, 30%, 35%, 40%, 45%, 50%, 55%, 60%, 65%, 70%, 75%, 80%, 85%, 90%, 95% or more compared to the activation or formation of TRPC channels that have not been exposed to the agent.

As used herein, the term "selectively inhibits" with reference to a TRPC4/5 inhibitor or antagonist means that the inhibitor or antagonist inhibits the formation, activation or activity of a recited TRPC channel but does not inhibit the formation, activation or activity of one or more non-recited channels. For example, a TRPC4/5 inhibitor or antagonist that selectively inhibits TRPC4/5 channels inhibits the formation, activation or activity of TRPC4/5 channels (including a isoform channels) but does not inhibit the formation, activation or activity of a TRPC1, TRPC2, TRPC3, TRPC6, or TRPC7 channel. In another example, a TRPC4/5 inhibitor or antagonist that selectively inhibits TRPC4/5 channels inhibits the formation, activation or activity of TRPC4/5 channels but does not inhibit the formation, activation or activity of TRPC1, TRPC2, TRPC3, TRPC6, or TRPC7 channels, or isoforms thereof.

As used herein the term "expression" may refer to expression of a polypeptide or protein, or to expression of a polynucleotide or gene, depending on the context. Expression of a polynucleotide may be determined, for example, by measuring the production of RNA transcript levels. Expression of a protein or polypeptide may be determined, for example, by immunoassay using an antibody(ies) that bind with the polypeptide.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery.

As used herein, a "subject" includes human and non-human animals, including, for example, non-human primates, monkeys, mice, cows, sheep, dogs, cats, horses, birds and pigs.

II. TRPC Channels

Mammalian transient receptor potential canonical channels are described as six-transmembrane (6-TM) cation-permeable channels. TRPC channels control the gating of voltage-dependent $Ca^{2+}$, $K^+$, and $Cl^-$, and are characterized as calcium-permeable channels with polymodal activation properties. TRPC protein structure is thought to be a channel forming structure composed of six transmembrane (TM) domains with a pore domain (P) located between the fifth (S5) and sixth (S6) TMs. TRPC channels are activated by three major mechanisms; receptor, ligand, and environment direct activation. Receptor activation is carried out by G protein coupled receptors (GPCRs) and tyrosine kinases in three modes which result in liberation of Ca2+ from intracellular stores: hydrolysis of phosphatidylinositol (4,5) bisphosphate (PIP2), diacylglycerol (DAG) and inositol (1,4,5) triphosphate (IP3). Ligand activation occurs by exogenous small molecules (capsaicin, icilin, 2-APB), endogenous lipids or metabolism products (diacylglycerols), purine nucleotides and metabolites (ADP-ribose), and inorganic ions. TRPC channels are also activated by environmental triggers such as ambient temperature.

The TRPC subfamily was established by the identification of the first mammalian TRP, TRPC1. Common TRPC motifs are composed of 2-3 ankyrin-like domain repeats and a coiled-coil domain in the N-terminal, followed by six transmembrane domains, the C-term TRPC box and a calmodulin (CaM) binding site. The CaM domain in TRPC4 is a calcium binding domain which resembles the CaM protein, which is normally small (~140+ amino acid in length) dumbbell-shaped composed of two structurally similar globular domains separated by a flexible hinge central helix. The globular domains are homologous and contain pairs of Ca2+ binding helix-loop-helix motifs which are referred to as the EF hand motifs. The typical mechanism of calcium binding occurs at these EF hands, which are composed of two a-helices linked to a 12-residue loop. The EF hand domains become exposed to effectors and targets by protein conformational change. The exposed hydrophobic regions in turn bind basic amphiphilic helices (BAA helices). The hinge of CaM allows for the proteins harboring a CaM domain to contact and activate targets. CaM is highly conserved in animals and plants and acts on many targets including ion channels.

TRPC4 and TRPC5 are highly homologous, and are highly expressed in the human brain, uterus, ovary and kidney cells. TRPC5 (Accession No. NC_005120.2) is expressed homomerically and heteromerically complexes with TRPC4 (Accession No. NC_005101.2). TRPC4 is a nonselective cation channel which is uniquely activated by $G_{q/11}$ family GPCRs through activation of PLCβ, and receptor kinases and receptor tyrosine kinases. Although studies using TRPC4 have shown that activation requires phospholipase C (PLC) activity, neither $IP_3$ nor DAG is sufficient to activate TRPC4. TRPC4 contains a PDZ-binding motif. PDZ domains are common structural motifs which aid proteins in signaling and anchoring transmembrane proteins to the cytoskeleton. PDZ domain scaffolding proteins, as well as signaling molecules, co-immunoprecipitate with TRPC4. PDZ domain is a common structural domain of 80-90 amino-acids found in the signaling proteins of bacteria, yeast, plants, viruses and animals. PDZ is an acronym combining the first letters of three proteins—post synaptic density protein (PSD95), Drosophila disc large tumor suppressor (DlgA), and zonula occludens-1 protein (zo-1)—which were first discovered to share the domain. PDZ domains are also referred to as DHR (Dlg homologous region) or GLGF (glycine-leucine-glycine-phenylalanine) domains. These domains help anchor transmembrane proteins to the cytoskeleton and hold together signaling complexes.

Almost every cell type scrutinized contains at least one TRPC channel. This large family of physiological important channels has been implicated in many human diseases. Most of the TRPC channels are conserved in mice, rats, and humans. Knockout mice studies have proven to be insightful for determining TRPC channel functions. Trpc2 deficient mice are unable to distinguish male from female counterparts and TRPV6 is upregulated in prostate cancer. TRPC4 transcripts and protein are expressed in primary cultured mouse vascular endothelial cells (MAECs) and the channels can be activated by store-depleted protocols in MAECs. In Trpc4 deficient mice, agonist induced $Ca^{2+}$ entry is significantly reduced. Trpc4-/- mice exhibit significant decrease in endothelium-dependent vasorelaxation in the blood vessels. The Trpc4 deficient mice display decreased microvascular permeability, and has altered GABA transmitter release from thalamic interneurons.

It has been proven that the human TRPC4 protein contains multiple ankyrin domains throughout and within the N-terminus along with a coiled-coil domain. The N-terminus of TRPC4 is very important for subunit assembly and pore formation. Two regions in the N-terminus are essential for channel assembly in TRPC channels and more specifically TRPC4; the third and fourth ankyrin repeats and the region downstream the coiled-coil domain. The second and third ankyrin repeats are represented by F59-S137 in TRPC4. Both domains are able to self-associate but have not been shown to interact with one another. These peptides have been identified to be involved in channel assembly of TRPCs and more specifically TRPC4. There are two domains in the TRPC4 protein that are responsible for oligomerization. The first domain contains the N-term ankyrin repeats and the coiled-coil domain (M1-P304) and the second domain corresponds to the putative pore region and the C-terminal tail (I516-L974). Two models exist in which the TRPC4 channel becomes functional upon subunit assembly. One model is that the third ankyrin repeat initiates a molecular zippering process. In this model each interacting domain would have the ability to tetramerize. In another model, the first interaction domain forms a dimer between two subunits and the second domain is responsible for the formation of a dimer between two other subunits. The N-terminal of both TRPC4 and TRPC5 including at least the first ankyrin repeat are essential for both homo and hetero-subunit assembly. TRPC4 protein homo and heteromeric pore formation is critical for protein function; therefore, agents that block TRPC4 multimeric formation are reasonable candidates for TRPC4 protein inhibitors.

III. TRPC4/5 Antagonists

An agent that inhibits TRPC4/5 channel formation, activation, or activity can be used in the methods and compositions described herein to inhibit or prevent brain injury associated with increased neuronal excitability. Inhibition of TRPC4/5 channel formation, activation or activity can be modulated by inhibiting TRPC4/5 expression and/or inhibiting TRPC4/5 activity (e.g., the ability of TRPC4/5 to form channels and facilitate cation flux).

TRPC4/5 inhibitors or antagonists include small molecules (e.g., chemical entities), proteins, and nucleic acid molecules that block or inhibit TRPC4/5 channel activation or formation. In some embodiments, the TRPC4/5 inhibitor or antagonist is specific for TRPC4/5 channels. In other embodiments, the TRPC4/5 inhibitor or antagonist is a non-specific inhibitor, such as a tyrosine kinase inhibitor, and inhibits the activation or formation of TRPC4/5 and one or more other TRPC channels, such as TRPC1, TRPC2, TRPC3, TRPC6, or TRPC7. In further embodiments, the inhibitor or antagonist is specific for TRPC4/5, such that other TRPC channels are unaffected or substantially unaffected by exposure to the inhibitor. The term substantially as used in this context refers to a change in activity of about or less than +/−10%.

In some instances, the TRPC4/5 inhibitors or antagonists or complexes or conjugates thereof used in the methods and compositions of the present invention can cross the blood brain barrier (BBB) to facilitate efficient delivery of the inhibitor to the TRPC4/5-expressing neurons. The BBB is often compromised in certain CNS diseases and conditions, such as epilepsy, and inhibitors that may not cross the BBB in healthy individuals can do so in individuals suffering brain injury. Specialized delivery methods also can be used to facilitate passage of an inhibitor across the blood brain barrier. Inhibitors can be engineered for receptor-mediated transport across the BBB by, for example, transferrin receptors, insulin receptors, and low-density lipoprotein receptors. In such instances, the inhibitor is linked to the endogenous ligands or monoclonal antibodies that bind these receptors to trigger transport across the BBB (see e.g., Pardridge and Boado (2012) Methods Enzymology 503: 269-292). Nanocarriers have also been shown to be able to deliver agents across the BBB (see e.g., Bhaskar et al. (2010) Part Fibre Toxicol. 7:3). Methods of temporarily permeabilizing the BBB also can be used. For example, administration of an adenosine receptor agonist has been shown to modulate BBB permeability and facilitate delivery of an intravenously injected antibody to the brain (Carman et al. (2012) J Neurosci. 31(37):13272-80). Other agents, including mannitol and bradykinin, as well as methods such as focused ultrasound, can also be used to temporarily disrupt the BBB and facilitate delivery of therapeutic agents to the brain (Etame et al. (2012) Neurosurg Focus. 32(1):E3).

In some embodiments, the TRPC4/5 inhibitor or antagonist used in the methods and compositions of the present invention is a small molecule, such as a chemical compound. Exemplary small molecules include, but are not limited to, xanthines such as Pico145 (HC-608, CAS No. : 1628287-16-0) and HC-070 (CAS No. 1628291-95-1); derivatives of benzimidazole and 2-aminobenzimidazole such as clemizole (442-52-4) hydrochloride, M084, and AC1903 (831234-13-0); 2-aminoquinolines such as ML204; inhibitors of calmodulin such as analogs of trifluoroperazine (TFP), arylalkylamine derivatives including fendiline, bisindole derivatives including vinblastine, navelbine, and an analog termed KAR-2, inhibitors derived from fungi including malbrancheamide, tajixanthone hydrate, and chlorpromazine (CPZ), melittin, and W-7; flavonols such galangin, a natural product from *Alpinia officinarum* and other members of the ginger family, and AM12; and the TRPC4 and 5 inhibitors described in EP2467398B1, WO2019051197A1, and WO2018146485A1, the contents of which is incorporated herein by reference.

In one embodiment, M084 hydrochloride ("M084"), which has been shown to efficiently cross the BBB, is used in the methods and compositions of the present invention. M084 (N-butyl-1H-benzimidazol-2-amine) is a well-characterized synthetic 2-aminobenzimidazole compound. M084 is a potent inhibitor or antagonist of TRPC4 and TRPC5, and a weak inhibitor or antagonist of TRPC3. It is a good pharmaceutical tool for investigating the physiological and pathophysiological functions of TRPC4/5 channels. Any form of M084 can be used in the methods of the present invention providing that form retains the ability to block TRPC4/5 channel activation or formation.

In another embodiment, ML204 is used in the methods and compositions of the present invention. ML204 (4-Methyl-2-(1-piperidinyl)quinolone) is a synthetic 2-aminoquinoline compound that has been shown to selectively inhibit TRPC4/5-mediated $Ca^{2+}$ influx, while demonstrating no appreciable blockage of other TRPC channels. Accordingly, ML204 or other TRPC4/5-specific inhibitors or antagonists can be used in embodiments of the present invention to specifically inhibit TRPC4/5-mediated $Ca^{2+}$ flux while not interfering with other TRPC channel activity.

TRPC4/5 inhibitors or antagonists for use in the present invention also include inhibitory nucleic acids, such as antisense oligonucleotides, ribozymes, miRNAs and siRNAs, that target TRPC4/5 transcripts. It is well within the skill of a skilled artisan to design and produce nucleic acid molecules such as antisense oligonucleotides, ribozymes, miRNAs and siRNAs that target TRPC4/5 transcripts. For example, siRNA molecules that target TRPC4/5 and inhibit TRPC4/5 channel formation are commercially available and known in the art. In some embodiments, only main isoform TRPC4/5 mRNA is targeted by the nucleic acid molecules.

In other instances, the nucleic acid molecules recognize and bind to all TRPC4/5 isoforms, inhibiting the formation of channels with any isoform.

The efficacy of the TRPC4/5 inhibitors or antagonists can be assessed using methods and assays well known in the art, including, for example, the assays described in the Examples below. For example, in vitro assays can be used to determine the effect of the inhibitor on $Ca^{2+}$ flux in neurons. In vivo assays using small animal models can be used to assess the effect of the inhibitor on neuroprotection following brain injury, such as brain injury associated with TBI and/or epilepsy.

IV. Formulation and Administration of TRPC4/5 Antagonists

TRPC4/5 inhibitors or antagonists can be formulated for in vivo use. For example, TRPC4/5 inhibitors or antagonists are formulated for administration to a subject. In certain embodiments, TRPC4/5 inhibitors or antagonists are formulated as pharmaceutical compositions and administered to a subject suffering from a CNS-associated disease or condition, such as stroke, epilepsy, severe blood loss and/or head trauma (such as a contusion or blunt force trauma, or other ischemic events), to inhibit excitability of neurons. Excitability of neurons can be inhibited in any region of the brain, including, but not limited to, the cerebellum, the midbrain, the cerebrum and/or the medulla. In certain aspects, hyperexcitability of neurons in the hippocampus is regulated by administration of a composition comprising a TRPC4/5 inhibitor.

Generally, compositions containing a TRPC4/5 inhibitor or antagonist are prepared in view of approval from a regulatory agency or otherwise prepared in accordance with generally recognized pharmacopeia for use in animals and in humans. Compositions can contain, in addition to the TRPC4/5 inhibitor or antagonist, a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. A pharmaceutical composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents.

The compositions can be formulated for administration by any route. The most appropriate route of administration can be determined by a person of skill in the art, taking into account the particular disease or condition being treated. For example, the compositions comprising a TRPC4/5 inhibitor or antagonist can be formulated for parenteral, intravenous, intraarterial, subcutaneous, intramuscular, intracranial, intraventricular, intranasal, or oral administration. In some embodiments, therapeutic formulations comprising TRPC4/5 are in the form of liquid solutions or suspensions for intravenous administration. Also encompassed by the present invention are formulations for controlled release of a TRPC4/5 inhibitor or antagonist.

The compositions comprising a TRPC4/5 inhibitor or antagonist are formulated with an amount or concentration of a TRPC4/5 inhibitor or antagonist that is suitable for the embodiments of the present invention, i.e., at concentrations or amounts sufficient to regulate the excitability of neurons when administered to a subject. The compositions can be formulated for direct administration to a subject or can be formulated as a concentrated composition that is subsequently diluted prior to use. The compositions can be formulated with between about 1 ng/mL to about 100 mg/mL of a TRPC4/5 inhibitor, between about 10 ng/mL and about 10 mg/mL, between about 100 ng/mL and about 10 mg/mL, between about 1 μg/mL and about 10 mg/mL, between about 10 μg/mL and about 1 mg/mL, or between about 100 μg/mL and about 1 mg/mL of TRPC4/5 inhibitor. In some instances, the compositions are in solid form, such as in tablet or capsule form, and contain the TRPC4/5 inhibitor at between about 0.001% (w/w) to about 50% (w/w), between about 0.01% (w/w) to about 20% (w/w), between about 0.5% (w/w) to about 10% (w/w), or between about 1% (w/w) to about 5% (w/w). The most suitable concentration to achieve the desired effect will depend on a number of factors and may be determined by those skilled in the art using routine experimentation.

The compositions comprising a TRPC4/5 inhibitor or antagonist can include one or more TRPC4/5 inhibitors or antagonists, including 2, 3, 4, 5, or more TRPC4/5 inhibitors or antagonists. The compositions comprising a TRPC4/5 inhibitor or antagonist can also contain one or more additional active agents. For example, the TRPC4/5 inhibitor or antagonist compositions provided herein can include one or more other active agents useful in the treatment or stabilization of subjects suffering from stroke, epilepsy, severe blood loss and/or head trauma.

The formulations can be administered to a subject in therapeutically effective amounts, e.g., amounts that regulate the excitability of neurons. The precise amount or dose of the TRPC4/5 inhibitor or antagonist that is administered to the subject depends on several factors, including, but not limited to, the activity of the inhibitor, the use of other therapeutic agents, the route of administration, the number of dosages administered, and other considerations, such as the weight, age, and general state of the subject. Dosages can be empirically determined or extrapolated from, for example, studies in animal models or previous studies in humans.

The compositions containing a TRPC4/5 inhibitor or antagonist can be administered by any method and route understood to be suitable by a skilled artisan, including, but not limited to, intravenous (including by discrete injection, intravenous bolus or continuous infusion), intramuscular, parenteral, intracranial, intraarterial, subcutaneous, intranasal, oral, or intraperitoneal, as well as by any combination of any two or more thereof, formulated in a manner suitable for each route of administration.

In the methods provided herein, a composition comprising a TRPC4/5 inhibitor or antagonist is administered to a subject before, during and/or after the subject has experienced an event that results in increased neuronal excitability in the brain. Exemplary of such events are strokes, epileptic seizures, head trauma, severe blood loss, cardiac arrest, and other ischemic events. A composition comprising a TRPC4/5 inhibitor or antagonist can be administered to a subject at any time after the subject has experienced an event that results in hyperexcitability, such as 1 minute, 5 minutes, 15 minutes, 30 minutes, 1 hour, 2 hours, 3 hours, 4 hours, 5 hours, 6 hours, 7 hours, 8 hours, 9 hours, 10 hours, 11 hours, 12 hours, 18 hours, 24 hours, 3 days, 4 days, 5 days, 6 days, 7 days, 2 weeks, 3 weeks, 4 weeks or more after the subject has experienced an event that results in increased neuronal excitability in the brain. The TRPC4/5 inhibitor or antagonist can be administered once or more than once, such 2, 3, 4, 5, 6 or more times.

For example a subject suffering an epileptic seizure can be administered a TRPC4/5 inhibitor or antagonist and an anticonvulsant agent. In such instances, the TRPC4/5 inhibitor or antagonist can be administered simultaneously and/or sequentially to the other therapy. For example, the TRPC4/5 inhibitor or antagonist can be administered to the subject at the same time, before and/or after a surgical procedure is performed on the subject. Similarly, the TRPC4/5 inhibitor or antagonist can be administered to the subject at the same time, before and/or after another therapeutic is administered to the subject. In embodiments where a subject is administered a TRPC4/5 inhibitor or antagonist and one or more other therapeutic agents, the TRPC4/5 inhibitor or antagonist and the one or more other therapeutic agents can be in the same or different compositions, and can be administered by the same or different routes.

In other embodiments of the present invention, the TRPC4/5 inhibitors or antagonists are exposed to cells in vitro, such as in assays to assess TRPC4/5 inhibitor or antagonist specificity and/or activity. The cells can be neurons or other cells, such as cells expressing recombinant TRPC4/5. In certain aspects, the cells exposed to a TRPC4/5 inhibitor or antagonist are also exposed to an activating agent that activates TRPC4/5 channels. Accordingly, also provided herein are methods in which a cell is contacted with or exposed to a TRPC4/5 inhibitor or antagonist. Typically, various parameters are then assessed, such as membrane conductance and cation flux.

Those skilled in the art will appreciate that the aspects and embodiments described herein are susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations of any two or more of said steps or features.

The citation of any reference herein should not be construed as an admission that such reference is available as "Prior Art" to the present application. Further, the reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavor to which this specification relates.

The present disclosure is further described by reference to the following non-limiting examples.

V. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 1B:
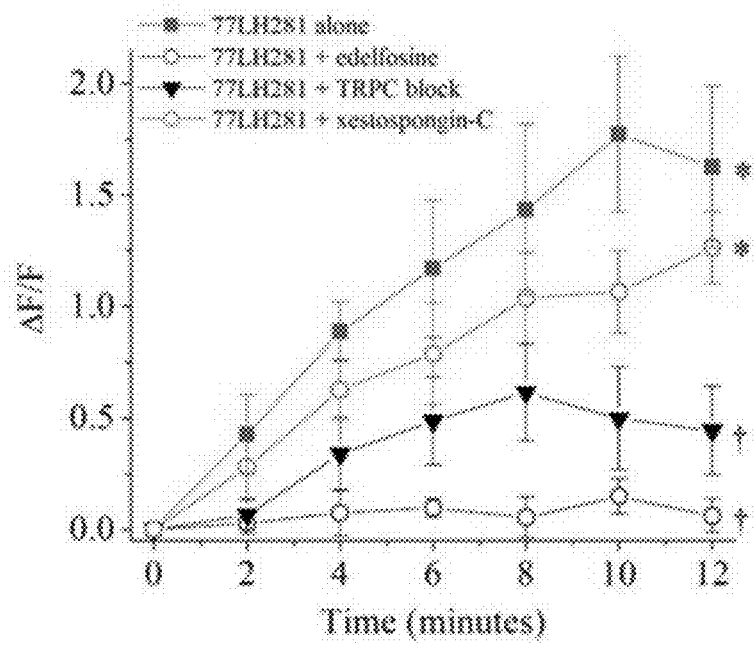
Figure 1C:
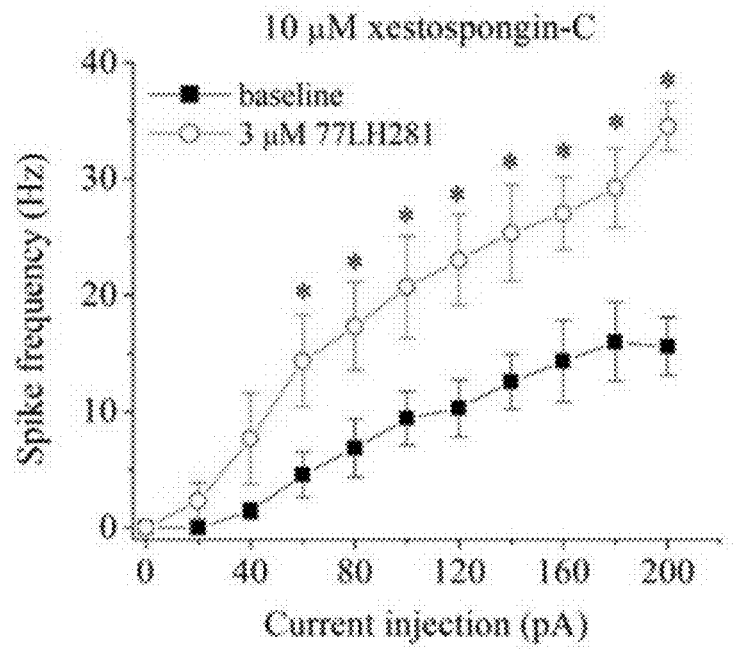

Stimulation of $G_{q/11}$-Coupled $M_1Rs$ of DGGCs Induces Increases in $[Ca^{2+}]_i$ Mostly via TRPC Channels, the Activity of Which Mediates Increased Excitability The inventors' data in DGGCs thus far indicate that $M_1R$ stimulation enhances $I_M$ amplitude, yet robustly increases active and passive excitability, conferring higher rates of action potential firing. The inventors hypothesized the involvement of another excitatory ion channel that would be activated downstream of $G_{q/11}$ activation and PLC. The inventors investigated whether stimulation of MiRs could provoke rises in $[Ca^{2+}]_i$ because such rises have been shown to be the determining factor in whether $G_{q/11}$-coupled receptor stimulation depletes $PIP_2$ in sympathetic neurons (Hernandez et al., 2008a,b). Indeed, cholinergic stimulation has been shown to increase $[Ca^{2+}]_i$ in the soma and mossy fiber axons of DGGCs (Itou et al., 2011). To investigate $[Ca^{2+}]_i$ dynamics of DGGCs in slices, the inventors performed $Ca^{2+}$ imaging in whole-cell mode with the cell-impermeant fluorescent reporter calcium-green 1 in the internal pipette solution (FIG. 1A). In response to $M_1R$ stimulation by 77-LH-28-1 (3 or 10 μm), peak fluorescence increased 2.91±0.41-fold or 4.27±0.95-fold, respectively (FIG. 1B). The $Ca^{2+}$ signal began to increase within 1 min after muscarinic agonist application to the slice, concurrent with the time at which granule cell action potential firing frequency increased, as well as enhancement of $I_M$ amplitude. $[Ca^{2+}]_i$ reached a maximum, as detected by dye fluorescent emission, 10 min after application of muscarinic agonist. Whereas calibration of the intensity dye is not feasible (Zhou and Neher, 1993), the inventors estimate, based on the inventors' previous work, that the maximum $[Ca^{2+}]_i$ rise to be well above 1 μm. When slices were preincubated with edelfosine (10 μm), 77-LH-28-1 had no significant effect on $[Ca^{2+}]_i$ (maximum dye emission=1.15±0.08-fold over that before agonist; FIG. 1A, 1B). An important question is whether these $[Ca^{2+}]_i$ rises evoked by muscarinic stimulation require the release of $Ca^{2+}$ from intracellular ER stores. To address this, the inventors repeated $Ca^{2+}$ imaging experiments using the $IP_3$ receptor inhibitor xestospongin C (10 μm) to block IP3 receptor-mediated release of $Ca^{2+}$ (Gafni et al., 1997). The inventors found that despite blockade of $IP_3$ receptors, mAChR stimulation still provoked substantial rises in $[Ca^{2+}]_i$ (FIG. 1A, 1B) and increase to DGGC hyperexcitability was still observed upon mAChR stimulation, as indicated by increased action potential firing frequency (FIG. 1C).

What excitatory ion channel could be activated downstream of mAChR-induced PLC activity, act as a source of sustained rise in $[Ca^{2+}]_i$, and induce marked increases in excitability of DGGCs? TRPC cation channels are activated by PLC-mediated signals (Strübing et al., 2001), permeant to $Ca^{2+}$ influx, and are known to be highly expressed in DG and hippocampus, consisting of TRPC1/4/5 heteromers (Chung et al., 2006a,b; Ramsey et al., 2006; Fowler et al., 2007; Wu et al., 2010; He et al., 2012; Bröker-Lai et al., 2017). These facts suggest a putative link for TRPC conductances to serve as a potent mechanism that could modulate neurotransmitters and excitability in brain via metabotropic receptors, similar to the regulatory control of M channels. Interestingly, TRPC channel opening is also facilitated by depletion of intracellular $Ca^{2+}$ stores (Boulay et al., 1999; see Discussion). Therefore, the inventors hypothesized TRPC channel contribution to the mAChR-induced hyperexcitability of DGGCs. Indeed, in the presence of saturating concentrations of TRPC4/5 blockers (M084 and ML204, 10 μm; Miller et al., 2011; Zhu et al., 2015), increases in $[Ca^{2+}]_i$ by muscarinic stimulation were mostly but not completely blunted, again, as detected by calcium-green 1 emission (maximum 1.61±0.21-fold; FIG. 1A, 1B).

Figure 1D:
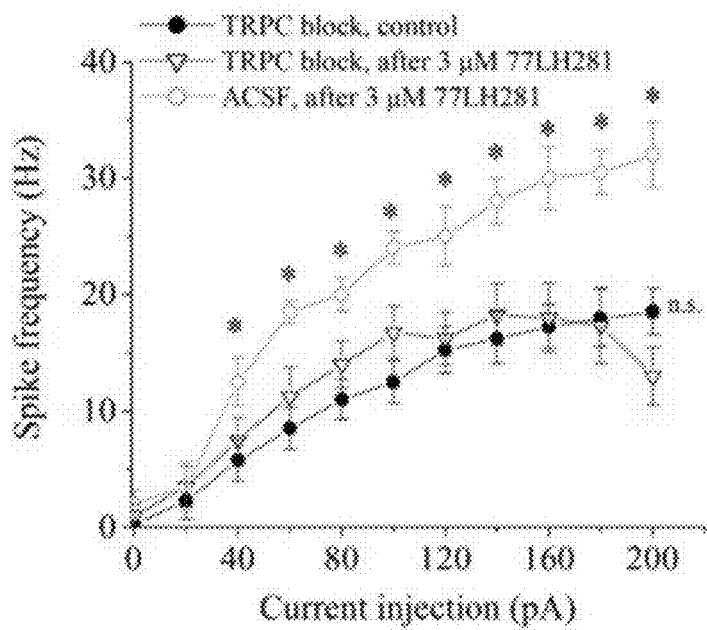
Figure 1E:
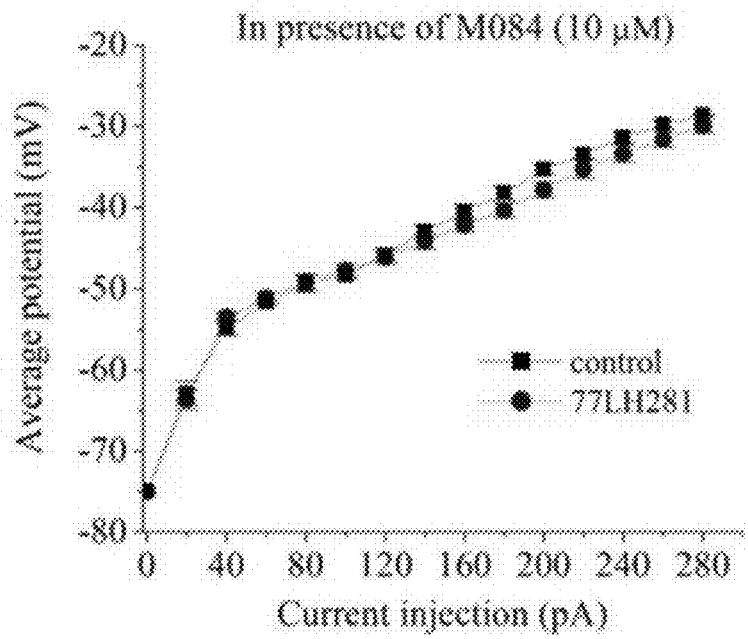

To further investigate whether activation of TRPC channels is the mechanistic basis for the muscarinic increase in DGGC excitability, the inventors performed parallel current-clamp recordings as before, comparing the muscarinic response in the presence or absence of the TRPC4/5 blocker M084 (10 μm). In this series of experiments, $M_1R$ stimulation with 77-LH-28-1 (3 μm) again significantly increased the action potential firing rate (FIG. 9D). However, under conditions of TRPC4/5 channel blockade, bath-application of MIR agonist did not increase the firing rate of action potentials (FIG. 1D and Table 1), nor was there a significant shift in the action potential threshold (M084 only: −45.4±1.3 mV, M084+77-LH-28-1: −46.1±1.5 mV, $t_{(14)}$=0.35, p=0.73, n=8 cells) or the average voltage floor across the range of voltages tested (FIG. 1E). However, blockade of TRPC channels did not prevent the enhancement of $I_M$ amplitude by $M_1R$ stimulation. With TRPC4/5 channels blocked, $M_1R$ stimulation (3 μm 77-LH-28-1) resulted in a 1.83 ±0.14-fold enhancement of $I_M$ amplitude (n=6 cells), which was similar to the enhancement observed in the absence of TRPC4/5 channel blockers (1.92±0.10-fold).

TABLE 1

Action potential properties derived from DGGCs during application of TRPC channel antagonists.

|  | Control (TRPC4/5 block) | 77-LH-28-1 (3 μM) |
|---|---|---|
| Initial interspike interval (Hz) | 10.9 ± 0.6 | 12.5 ± 1.0 |
| AP width (mV) | 4.2 ± 0.1 | 4.3 ± 0.1 |
| AHP decay (ms) | 14.8 ± 0.7 | 17.1 ± 0.8* |
| AHP amplitude (mV) | 13.2 ± 0.7 | 13.6 ± 0.9 |
| AHP area (ms* mV) | 196.8 ± 13.3 | 264.8 ± 21.5* |

*p < 0.05

Analysis of AP properties during current injection with TRPC4/5 channels blocked revealed increases in the decay time constant of the AHPs induced by MIR stimulation (14.8±0.6 vs 17.1±0.8 ms, $t_{(10)}$=2.30, p=0.044, n=6 cells) and in the mean area of the AHPs (197±11 vs 265±22 ms*mV, $t_{(10)}$=2.76, p=0.02), again, consistent with $M_1R$-mediated potentiation of $I_M$ (Table 1). However, with TRPC4/5 channels blocked, stimulation of MiRs had no significant effect on either parameter at each value of injected current, consistent with no change to excitability under those conditions (FIG. 1E). The inventors wondered whether there were microdomain-localized $Ca^{2+}$ signals mediated by IP$_3$Rs driving stimulation of PIP$_2$ synthesis, as has been proposed in sympathetic ganglia (Delmas and Brown, 2002; Winks et al., 2005; Zaika et al., 2007). However, inclusion of xestospongin C (10 μm) in the pipette, as before, retained $M_1R$-mediated enhancement of $I_M$ (1.67±0.14-fold, n=8 cells).

The inventors' findings are consistent with the inventors' hypothesis of TRPC4/5 (likely coupled with TRPC1) activation downstream of activation of PLC and PIP$_2$ hydrolysis, mediating at least most of the increased excitability of DGGCs upon muscarinic stimulation that has been observed by us and by others. The inventors note here that such stimulatory input must be quite strong because it opposes and clearly overwhelms the decrease in excitability that should otherwise occur upon enhancement of $I_M$. Feedback rises in $[Ca^{2+}]_i$ corroborate the likelihood of this scenario (Ordaz et al., 2005). However, the contribution of PLC-produced diacylglycerol (DAG) in particular remains unclear given previous evidence of inactivation of TRPC4/5-containing channels by DAG (Venkatachalam et al., 2003). With PIP$_2$ synthesis increased by several-fold upon muscarinic stimulation, production of DAG and its density in the membrane should correspondingly increase as well. The TRPC4/5-activated augmentation of the excitatory drive of DGGCs would thus be the result of the combinatorial actions of $M_1R$-mediated stimulation of PIP$_2$ synthesis, amplified PLC-mediated PIP$_2$ hydrolysis, release of $[Ca^{2+}]_i$, and subsequent feedforward amplification of TRPC channels (Fowler et al., 2007).

Figure 1F:
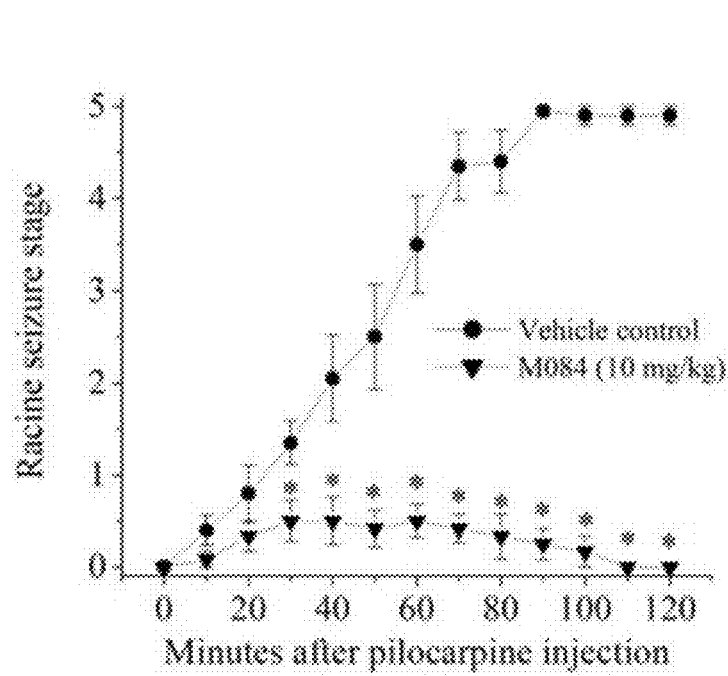

The hyperexcitability that the inventors ascribe to activation of TRPC4/5 channels by MIR stimulation in DGGCs led us to wonder whether TRPC4/5 channels could be key regulators of the spread of epileptogenic seizures. Prior evidence suggests the involvement of TRPC family channels in the control of excitability in other distinct neurons in the hippocampus (Strübing et al., 2001; Michel et al., 2005; Tai et al., 2011; Bröker-Lai et al., 2017). Moreover, TRPC4/5 blockade has been demonstrated to suppress depression-like and anxiety behaviors of mice in vivo (Yang et al., 2015), similar to profiles of several classes of anticonvulsant drugs with mechanisms of action that target neuronal inhibition. the inventors' $Ca^{2+}$-imaging experiments showed that TRPC4/5 blockade ablates most of the $M_1R$-induced rise in $[Ca^{2+}]_i$, suggesting that global TRPC4/5 blockade in the brain might preclude seizures mediated by undue $Ca^{2+}$ influx. To test this hypothesis in vivo, the inventors investigated TRPC4/5 channel block in the prevention of chemoconvulsant-induced seizures in mice using the well-established pilocarpine seizure model (FIG. 1F). This model has the advantage of widespread muscarinic receptor stimulation as the trigger for spreading hyperexcitability. After administration of scopolamine (1 mg/kg), control mice were pretreated with saline vehicle and then were administered pilocarpine (280 mg/kg) 30 min later. All control animals developed strong progression of seizures that resulted in status epilepticus (mean maximum Racine seizure stage: 4.8±0.2). However, littermates that were treated with the TRPC4/5 antagonist M084 (10 mg/kg) 30 min before the same dose of pilocarpine demonstrated significantly reduced seizure behavior (mean maximum Racine seizure stage: 1.1±0.5) and status epilepticus was not observed in any animal (n=8 mice per group; FIG. 1F). Because TRPC4/5 blockade suppressed chemoconvulsant seizures throughout the brain in this assay, these results are suggestive of a widespread role of TRPC channels in epileptogenesis (Zheng, 2017). Therefore, TRPC channel inhibitors may represent a mode of anticonvulsant therapeutic control of seizures and retardation of the development of epilepsy disease from a variety of causes.

Hippocampal Slice Preparation. Transverse slices (300 μm) of hippocampus were cut with a vibratome (Thermo Scientific, Microm HM650V) from mice using standard techniques with minor modifications, as reported previously (Carver et al., 2014). Mice were anesthetized with isoflurane and brains excised and placed in artificial CSF (ACSF) at 3.5 ° C. composed of the following (in mm): 126 NaCl, 3 KCl, 0.5 CaCl$_2$, 5 MgCl$_2$, 26 NaHCO$_3$, 1.25 NaH$_2$PO$_4$, 15 glucose, and 0.3 kynurenic acid, with pH adjusted to 7.35-7.40, with 95% $O_2$-5% $CO_2$, 305-315 mOsm/kg. Hippocampal slices were maintained in oxygenated ACSF at 30° C. for 60 min and experiments were performed at 25° C.

$Ca^{2+}$ Imaging. Concurrent with patch-clamp electrophysiology, neurons in slices were also imaged (Nikon FN-1, 40× water-immersion objective) via the fluorescent $Ca^{2+}$-reporter dye calcium green-1. As a hexapotassium salt, the dye (10 μm) was added to the intracellular patch pipette solution and neurons were patched under whole-cell clamp, as described above. Cells were loaded for 10 min before image acquisition. Fluorescence intensity was obtained using a SOLA Light Engine illumination source (Lumencor) with an output of 3.5 W through a 3-mm-diameter liquid light guide through a Nikon ET-GFP filter. Nikon Elements software was used for image acquisition through a QIClick CCD camera (QImaging). Images were acquired with an exposure time of 200 ms every 2 min using a single-channel, 12-bit rate and no binning. The shutter was closed between each acquisition. For each cell, the corrected total cell fluorescence was measured as the integrated density intensity—(cell area*mean background emission). $Ca^{2+}$ signals were measured as the change in fluorescence relative to the baseline fluorescence (ΔF/F0). Averages of four images were thresholded at 10%, masked using a highly averaged image of the cell, and encoded with a pseudocolor look-up table. Group cell fluorescence data were averaged in comparison with normalized intensity at each time point.

Behavioral Seizure Studies. The muscarinic agonist pilocarpine was used to induce seizures in vivo. Two-month-old mice were injected with scopolamine methylnitrate (1 mg/kg; MP Biomedicals) to block peripheral mAChRs 30 min before administration of pilocarpine hydrochloride (280 mg/kg; Sigma-Aldrich). Drugs were delivered via intraperitoneal injection in 0.9% sterile saline at a total volume equivalent to 1% of the mouse body weight. Control mice were given the same dose of scopolamine followed by vehicle saline 30 min later. Mice were observed for 2 h and all seizure activity was visualized and scored in severity according to the modified Racine scale for mice (Racine, 1972). Within 15 min, mice exhibited continuous tremor activity and tail rigidity. Peak seizure activity was observed 60 min after pilocarpine delivery with occasional forelimb clonus.

Drugs. Kynurenic acid, E-4031, ICA-069673, ZD7288, ML204, and M084 were from Tocris Bioscience.

Example 2

TRPC 4/5 Channels are Differentially Regulated in Brain after CCI-TBI

Figure 2A:
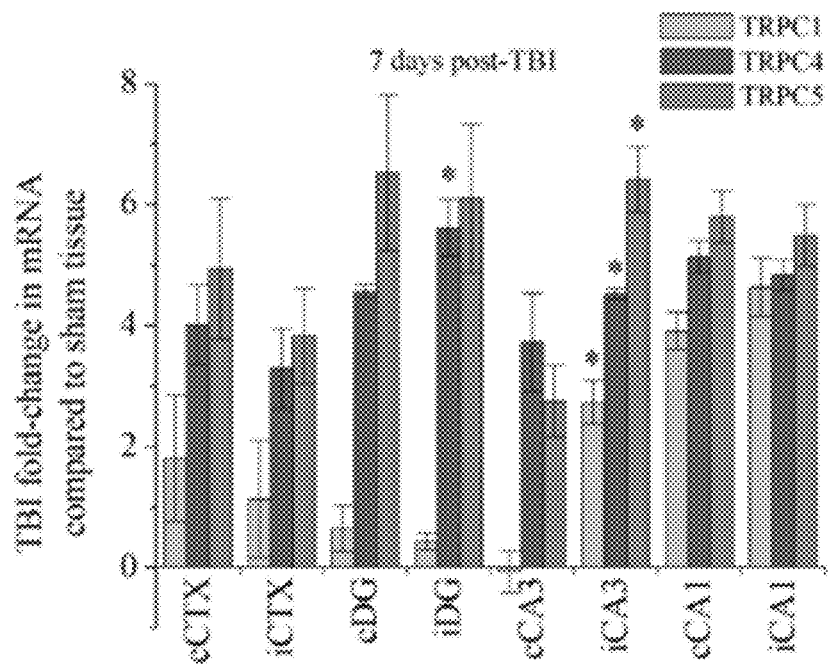
FIG. 2A-2E. Cell-type specific TRPC1, 4, 5 channel upregulation in hippocampus and cortex after CCI-TBI.

CCI-TBI was performed on adult mice in the investigation of neuronal hyperexcitability. It was hypothesized that TBI induces TRPC 1/4/5 channel plasticity in neurons. TRPC1, TRPC4, and TRPC5 mRNA expression between sham-surgery control mice and TBI mice were compared using quantitative real-time PCR in micro-dissected tissue 7 days after the procedure. In sham animals, there were no significant differences in mRNA between contralateral (left) and ipsilateral (right) brain tissue in the regions of hippocampus (CA1, CA3, DG) or parietal cortex. Conversely, an at least 3-fold average increase to both TRPC4 and TRPC5 mRNA from all tested regions of TBI brains in comparison to sham mice was observed (FIG. 2A). The CA1 region from TBI mice showed bilateral upregulation of TRPC1 mRNA. Ipsilateral CA3 also displayed significant increase in TRPC1, whereas DG and cortex did not exhibit changes in TRPC1 (FIG. 2A). In comparison of the hemispheres from TBI mice, DG and CA3 had significantly greater TRPC4 mRNA in the ipsilateral region compared to contralateral region, and CA3 had greater TRPC5 mRNA ipsilaterally as well.

Figure 2B:
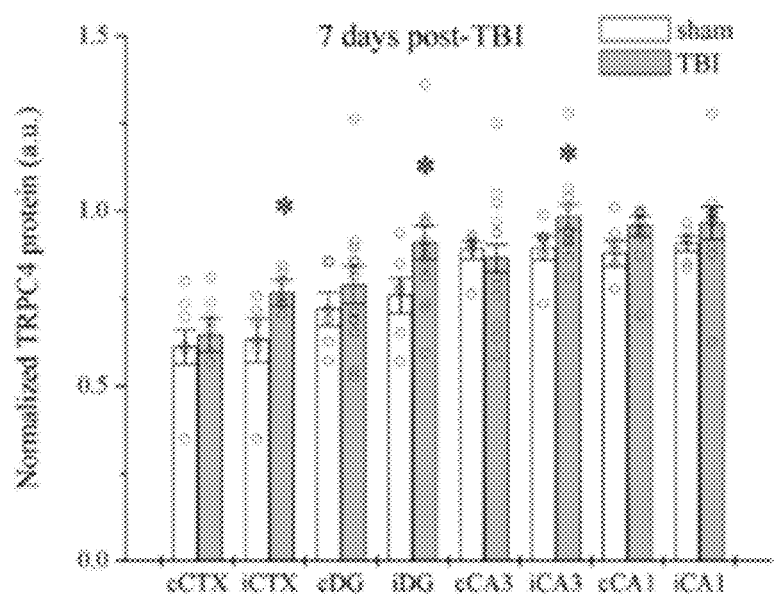
Figure 2C:
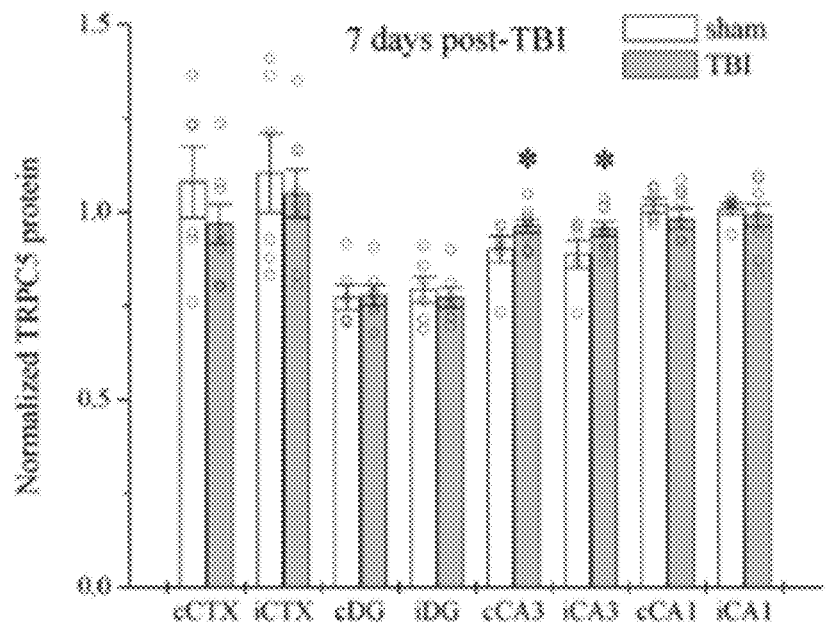
Figure 2D:
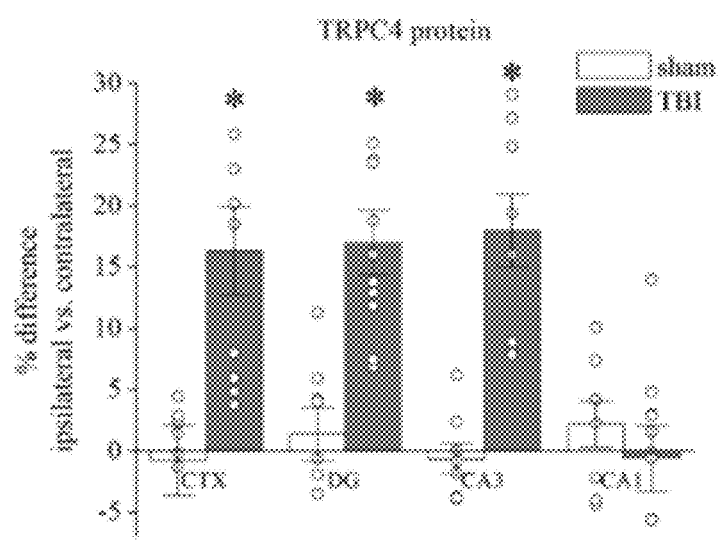
Figure 2E:
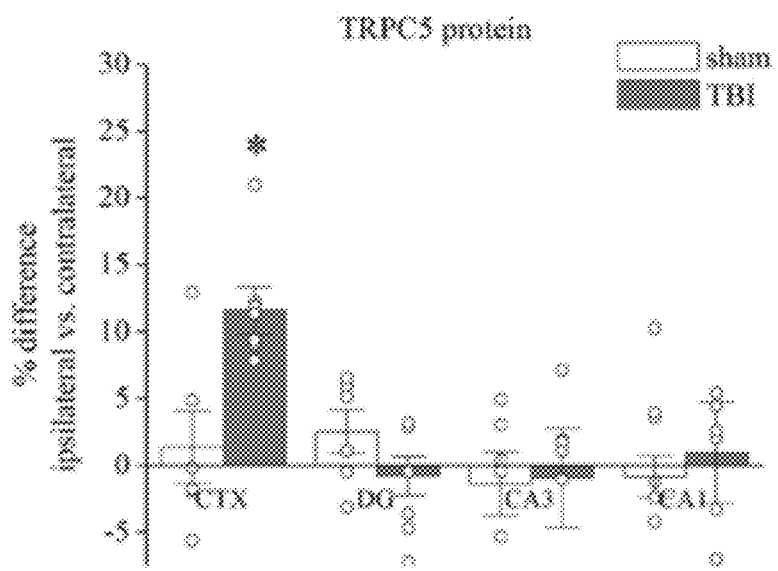

To determine if the observed upregulation of mRNA conveyed changes in channel protein after TBI, Western immunoblots of TRPC channels were analyzed at 7 days after TBI (FIG. 2B-2E, Table 2). Each of the cortex, DG, and CA3 ipsilateral regions from TBI mice exhibited significant increases in TRPC4 protein compared to the contralateral TBI tissue (FIG. 2B, 2D). However, TRPC5 protein levels were not significantly different between the hemispheres of TBI mice (FIG. 2C, 2E).

TABLE 2

Normalized TRPC4/5 protein in 7-day sham and TBI mice as represented in FIG. 2B-2C.

| Region/Protein | Contralateral sham [n] | Ipsilateral sham [n] | Contralateral TBI [n] | Ipsilateral TBI [n] |
| --- | --- | --- | --- | --- |
| CTX TRPC4 | 0.61 ± 0.05 [6] | 0.63 ± 0.06 [6] | 0.64 ± 0.04 [9] | 0.77 ± 0.03** [8] |
| CTX TRPC5 | 1.08 ± 0.09 [6] | 1.10 ± 0.10 [6] | 0.97 ± 0.05 [8] | 1.05 ± 0.06 [8] |
| DG TRPC4 | 0.72 ± 0.05 [6] | 0.78 ± 0.06 [6] | 0.79 ± 0.05 [12] | 0.91 ± 0.05* [12] |
| DG TRPC5 | 0.77 ± 0.03 [6] | 0.79 ± 0.03 [6] | 0.78 ± 0.03 [7] | 0.77 ± 0.03 [7] |
| CA3 TRPC4 | 0.89 ± 0.03 [6] | 0.89 ± 0.04 [6] | 0.86 ± 0.04 [12] | 0.98 ± 0.04* [12] |
| CA3 TRPC5 | 0.90 ± 0.04 [6] | 0.89 ± 0.04 [6] | 0.96 ± 0.02* [7] | 0.95 ± 0.02* [7] |
| CA1 TRPC4 | 0.88 ± 0.04 [6] | 0.91 ± 0.02 [6] | 0.96 ± 0.03 [12] | 0.96 ± 0.05 [12] |
| CA1 TRPC5 | 1.02 ± 0.02 [6] | 1.01 ± 0.01 [6] | 0.98 ± 0.03 [7] | 0.99 ± 0.04 [7] |

Protein values are normalized to β-actin and are listed as arbitrary units.
10 μg total protein were loaded for each sample.
Sample size n is listed in brackets beside each group and region.
*p < 0.05 vs. sham of same group,
**p < 0.01 vs. sham of same group, with unpaired two-tailed t-test.

Ipsilateral DG (p=0.030, n=6-12), ipsilateral CA3 (p=0.041, n=6-12), and ipsilateral cortex (p=0.016, n=6-8) from TBI mice exhibited significantly greater TRPC4 protein than the equivalent regions from sham mice (FIG. 2B). In analysis of TRPC5 protein, contralateral CA3 (p=0.028, n=6-8) and ipsilateral CA3 (p=0.041, n=6-8) of TBI mice had significantly greater protein levels than shams (FIG. 2C). To better understand the relative degree of TRPC channel protein change due to TBI, the percent difference in TRPC4/5 protein levels between contralateral and ipsilateral region of each mouse was analyzed, and the relative change between sham and TBI mice was compared. Similar to the data above, the ipsilateral cortex, DG, and CA3 regions from TBI mice showed significant increase in TRPC4 protein (FIG. 2D). Contralateral and ipsilateral cortex of TBI exhibited significant differences in TRPC5 (11.6±1.8% change), however, contralateral cortex TRPC5 was actually lower than baseline sham and ipsilateral cortex levels were similar to sham mice. The pooled data of contralateral and ipsilateral TRPC5 protein were not significantly different, and there was a greater variability between mice (FIG. 2E). Therefore, the difference in TBI cortical TRPC5 is likely due to a marginal decrease in contralateral TRPC5. CA3 had no difference in TRPC5 between TBI hemispheres (FIG. 2E), however both sides showed upregulation after TBI. Overall, the protein expression of TRPC4/5 in 7 day post-TBI mice was consistent with the mRNA expressional data we acquired. However, in comparison of control and TBI mice, the detected mRNA fold-change in expression was substantially larger than the tangible protein measured.

Figure 3A:
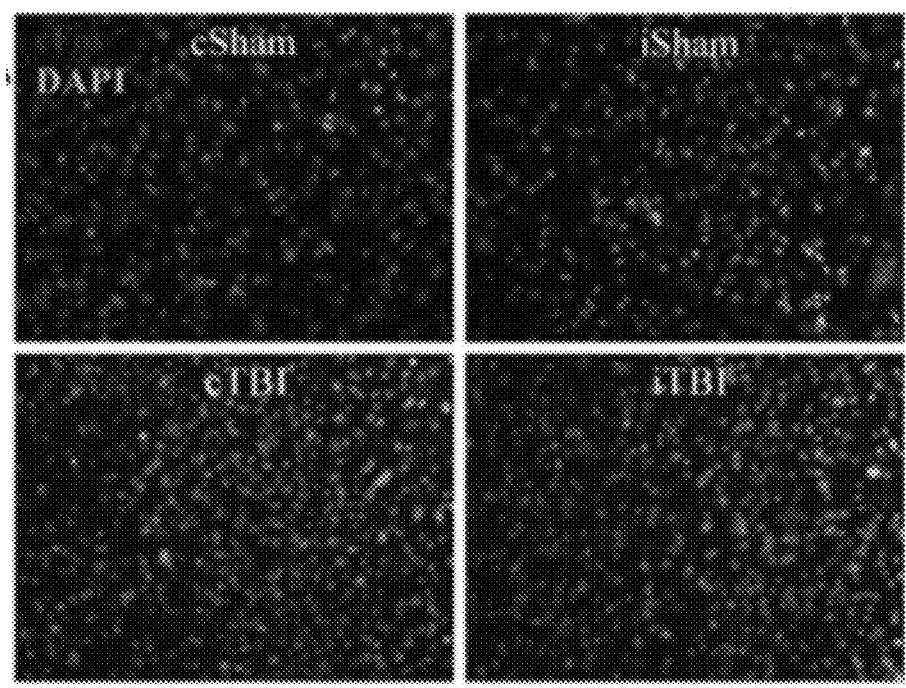
FIG. 3A-3E. Surges in neuronal activity and metabolic stress following CCI-TBI that are TRPC4/5-mediated.
Figure 3B:
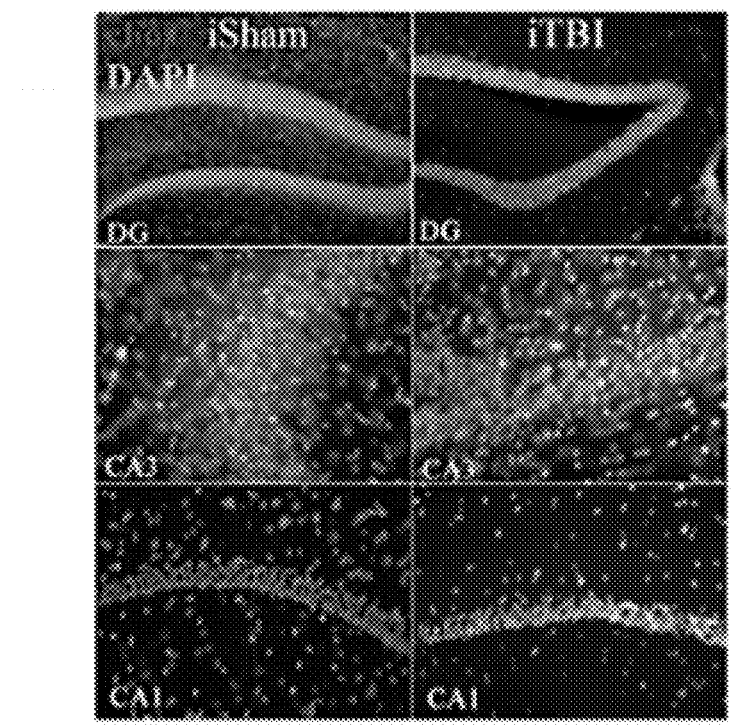
Figure 3C:
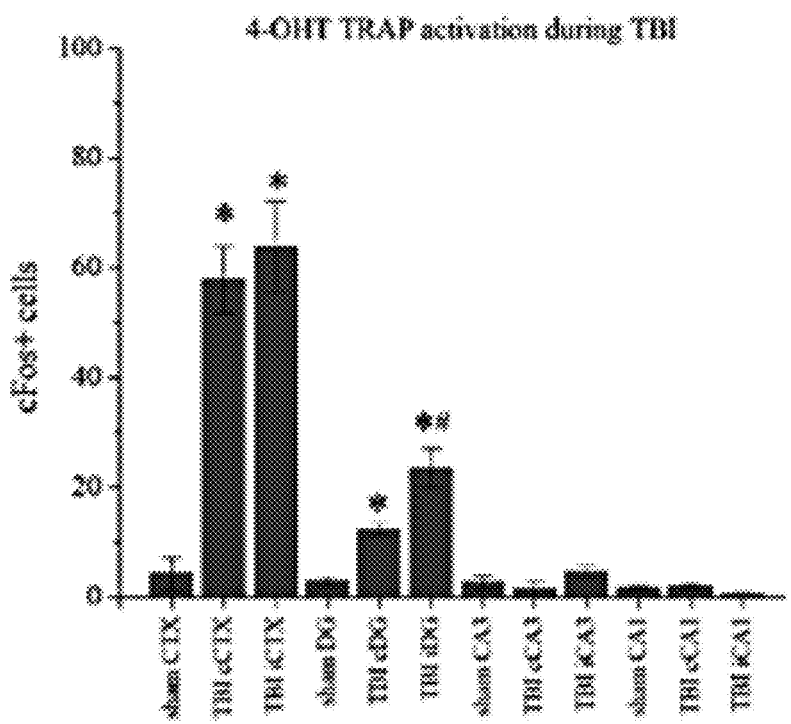

Post-traumatic effects of neuron-specific stress and hyperexcitability. Traditional studies of the TBI induction of neuronal activity are confined by a single snapshot at the time of animal sacrifice to study histological factors, including cFos immunoreactivity. As an immediate/early gene, cFos is only transiently active for 2-3 hours after brain insult until the signal can no longer be detected (Yang et al., 1994; Peng and Houser, 2005; Barros et al., 2015). To visualize and quantify the real-time neuronal activity in response to TBI, we used mice containing the transgene construct for cFos-TRAP, Targeted Recombination in Active Populations (Guenther et al., 2013) (FIG. 3). In TRAP mice, when conditionally activated with 4-hydroxytamoxifen (4-OHT), neurons expressing cFos/CreERT2 will produce and maintain the presence of recombinantly active td-Tomato fluorescent marker, thereby enabling detection of overall neuronal activity within a window of time in vivo (FIG. 3A). Therefore, we are able to quantify the percentage of cell-type specific neurons per volume (0.44 mm×0.33 mm×0.2 mm, or 0.307 $mm^3$) that are active in response to TBI. We administered 50 mg/kg 4-OHT to TRAP mice and performed TBI or sham surgery 12 hours later (FIG. 3A-3C). In sham mice, basal activity of cortical neurons was relatively low, with only 1 or 2 td-Tomato-positive neurons per field (FIG. 3C). In contrast, there were significant increases in td-Tomato cortical neurons from TBI mice, indicative of robust cFos activity compared to basal quiescence in the sham animals (FIG. 3A, 3C). The DG also had a notable increase in cFos+ neurons bilaterally in TBI mice (n=5 mice) (FIG. 3B). Due to the pervasive spread of the td-Tomato fluorophore within the cell, the TRAP-activated neurons' dendritic processes were illuminated as well, indicative of robust neuronal excitation.

Figure 3D:
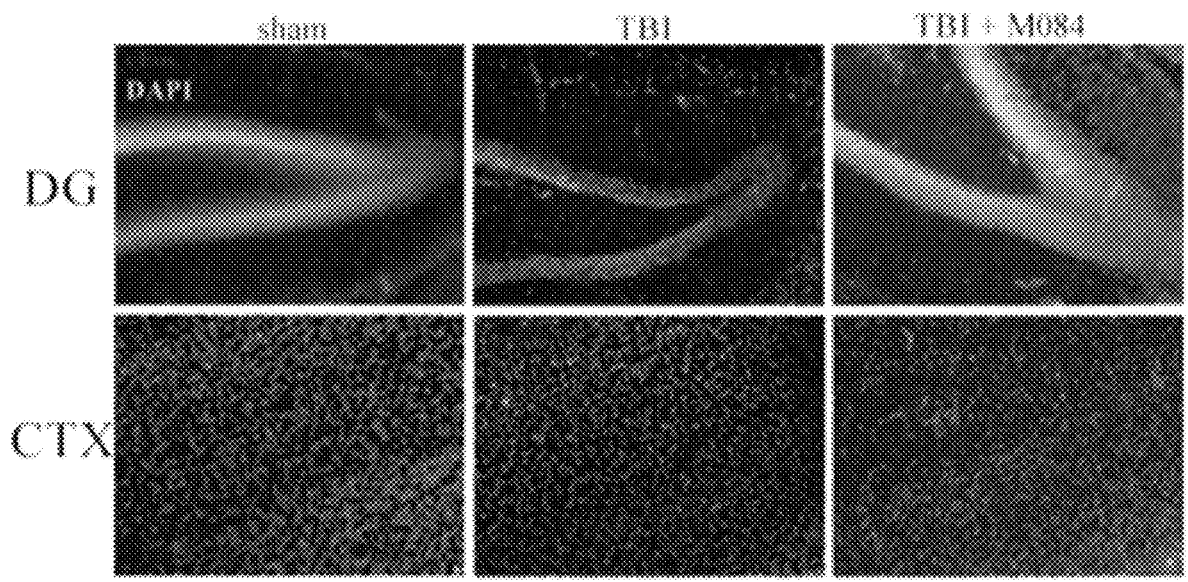
Figure 3E:
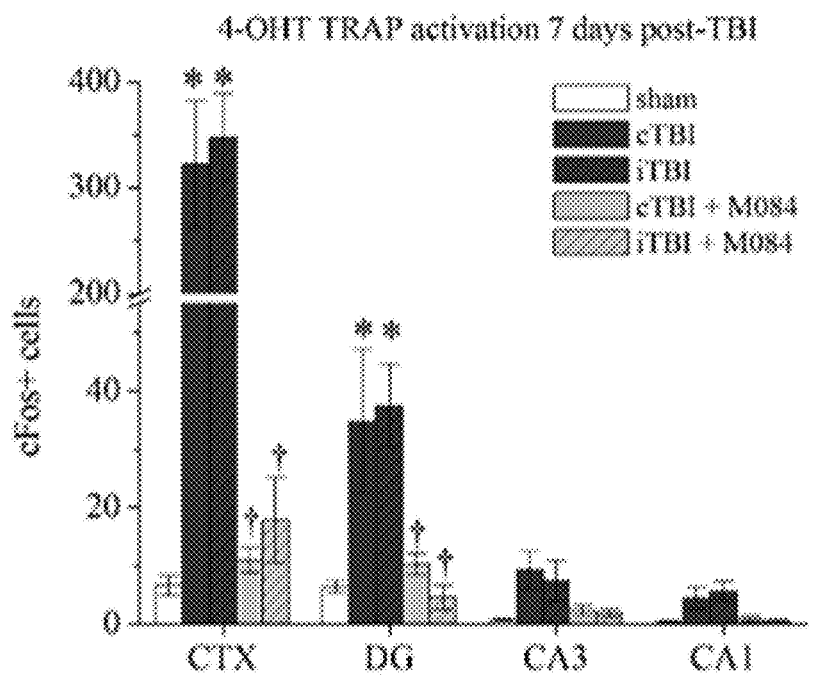

TRPC4/5 antagonism reduces TBI-induced neuronal hyperexcitability in cortex and dentate gyrus. We wished to determine if blockade of TRPC4/5 channels with M084 would decrease TBI-dependent neuronal activity. In a time-delayed study, we administered 4-OHT to TRAP mice at 7 days after sham or TBI condition (FIG. 3D-3F). This timing coincided with the period of significant TRPC4 upregulation after TBI (FIG. 2). A group was administered M084 (10 mg/kg) twice-daily for 7 days after TBI to create a steady-state concentration condition in the brain in maintenance of TRPC4/5 channel blockade (Yang et al., 2015). In anticipation of this injection regimen, the parallel cohorts of sham and TBI mice were administered vehicle on the same schedule. In visualization of cFos-active neurons, the 7-day sham hippocampus and cortex had nominal cFos activity, similar to the previous group of shams in FIG. 3A-3C. Sham animals typically displayed 0 or 1 active neurons in each regional slice of CA3 and CA1, whereas the 7-day TRAP TBI mice exhibited a small increase of cFos activation in CA1 and CA3 pyramidal neurons (FIG. 3D). We observed overt increases to cFos+principal neuron populations in both the DG and cortex of the untreated TBI mice (FIG. 3E). Conversely, mice treated with M084 exhibited sparse cFos activation, and cFos+ neurons were significantly fewer than in untreated TBI mice (FIG. 3E). Therefore, the neuronal activity induced by TBI was diminished by the blockade of TRPC4/5 channels in DG and cortex.

Neuromodulation of TRPC generates robust $Ca^{2+}$ influx and facilitates neuronal hyperexcitability. Upon observation of region-specific TRPC upregulation in neurons, we hypothesized this plasticity promotes hyperexcitatory activity in the post-traumatic hippocampus. We previously described that Gq/11-coupled M1Rs evoke persistent $Ca^{2+}$ influx, in part through TRPC channels, which contributes to DGGC excitability (Carver and Shapiro, 2019). To assess the post-injury effect of TRPC channel upregulation on neurons, we used $Ca^{2+}$ imaging in brain slice to measure excitability as a product of intracellular $Ca^{2+}$ gating by TRPC1/4/5 channels (FIG. 4). Due to robust increase in TRPC4 observed within the dentate gyms after TBI, we focused investigation on DGGC activity. Transgenic mice with the GCaMP6f transgene were used to detect changes in cellular $Ca^{2+}$-activated fluorescence. We hypothesized that DGGC activity increases due to muscarinic stimulation with ACh or direct activation of TRPC4-containing channels with EA. Sensitivity was tested by bath perfusion of ACh or EA to the slice for 5 minutes during $Ca^{2+}$ imaging to quantify peak amplitude of GCaMP6f fluorescence per cell, duration of $Ca^{2+}$ influx, and the field-frequency of events (FIG. 4).

Figure 4A:
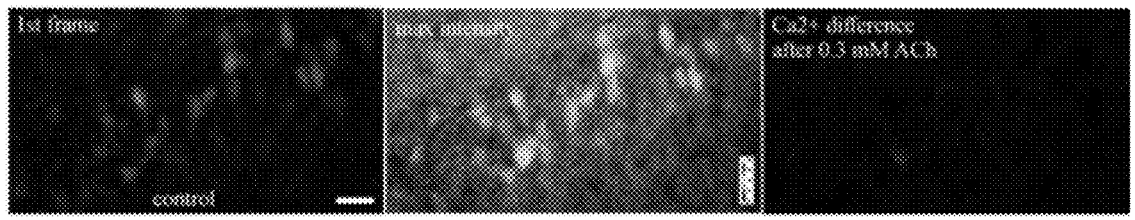
FIG. 4A-4E. TRPC-dependent cholinergic $Ca^{2+}$ influx in brain slice subsequent to CCI-TBI. Representative GCaMP6f $Ca^{2+}$ activity images from the DGGC layer of live brain slices for (FIG. 4A) control sham mice, (FIG. 4B) contralateral DGGCs to TBI (cTBI), and (FIG. 4C) ipsilateral DGGCs to TBI (iTBI) 7 days after procedure. Left image: showing the first frame of recording; Middle Image, the maximum intensity value for each pixel of $Ca^{2+}$ imaging after application of 0.3 mM ACh; Right Image: The composite difference in fluorescence intensity in comparing all frames to the first frame. Higher green fluorescence denotes greater $Ca^{2+}$ influx activity. GCaMP6f fluorescence intensity (ΔF/F) of DGGCs over time of bath application of 0.3 mM ACh. Experiments were carried out in the presence of hexamethonium chloride (50 μM) and TTX (1 μM).
Figure 4B:
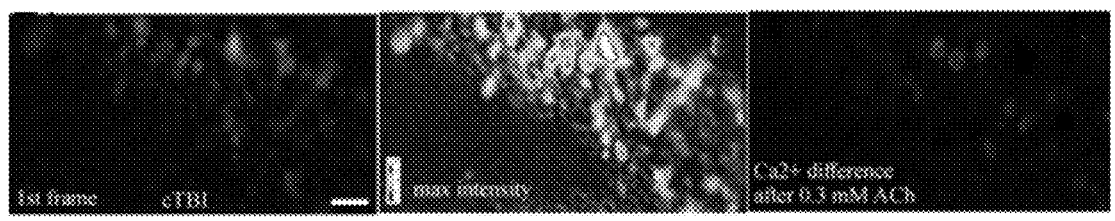
Figure 4C:
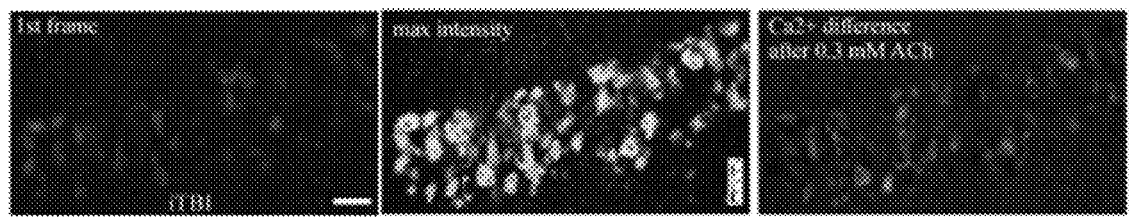
Figure 4D:
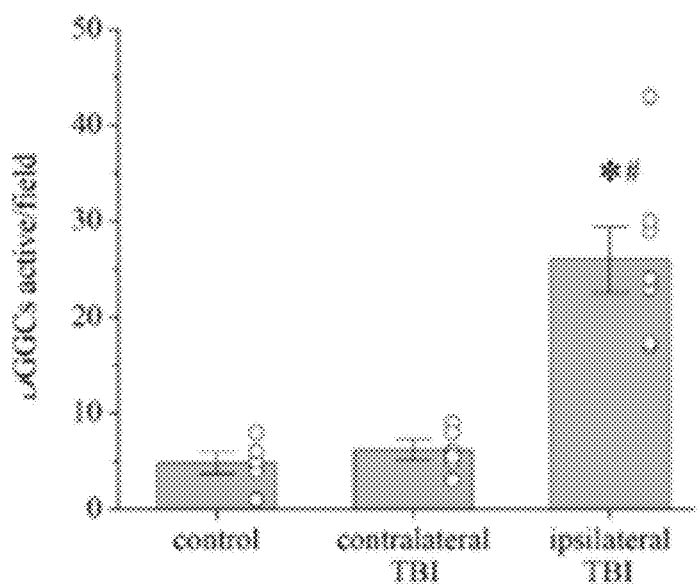
Figure 4E:
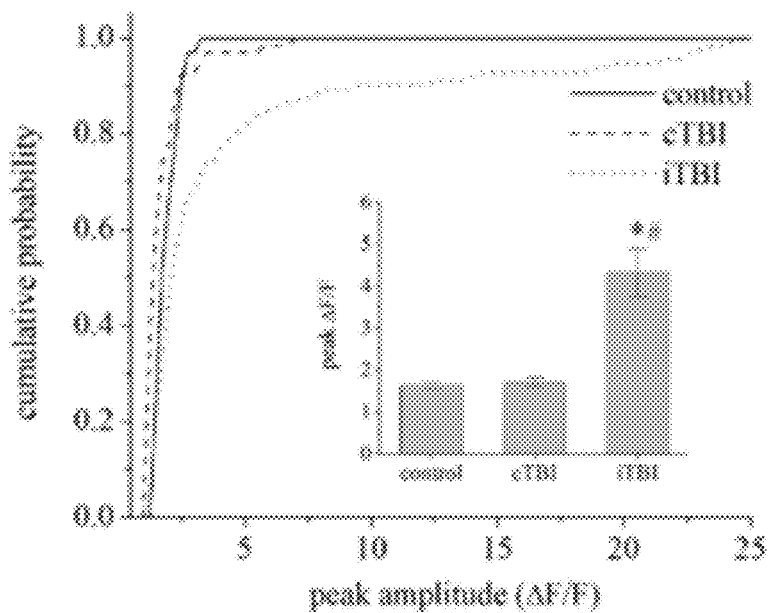
Figure 4F:
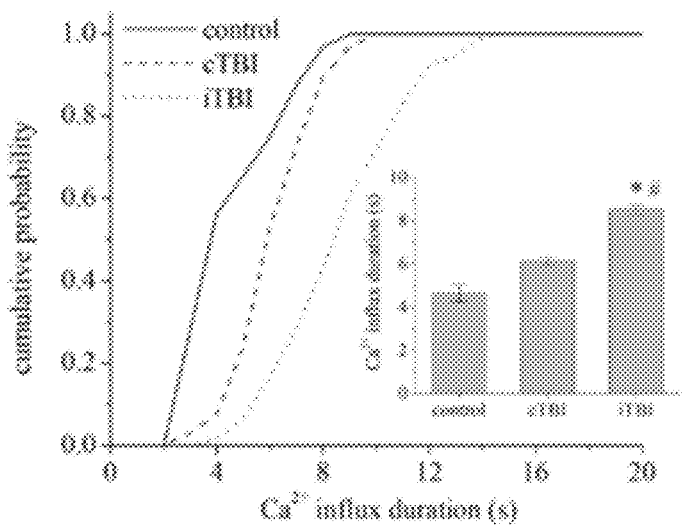
(FIG. 4F) Cumulative probability distribution of the $Ca^{2+}$ influx duration (in seconds) for each DGGC from control, cTBI, and iTBI slices. E-Insert: summarized mean data of $Ca^{2+}$ influx duration. All data bars represent the mean ±S.E.M. * p<0.05 vs. control, #p<0.05 vs. cTBI. Scale bars: 20 μm, 40× magnification with aqueous-immersed objective.

In sham animal recordings, intracellular $Ca^{2+}$ influx events were non-transient, with an average duration of 4.6±0.4 seconds per event and a 10-90% rise-time of 1.1±0.1 seconds. Bath application of 0.3 mM ACh (in presence of 50 μM hexamethonium chloride to block nAChRs) increased $Ca^{2+}$ activity in DGGCs from TBI mice, as compared with sham controls (FIG. 3A-3F). The $Ca^{2+}$ influx persisted in the presence of 1 μM TTX, and was therefore action-potential independent. Higher frame rate captures (240 Hz) demonstrated that the ACh-dependent $Ca^{2+}$ influx involved gradual increase to a single peak before subsiding, rather than displaying bursting behavior. The changes to $Ca^{2+}$ fluorescence were at slower intervals than the capabilities of GCaMP6f kinetics, therefore denoting the absence of temporal spiking dynamic in cholinergic stimulation. From TBI mice, ipsilateral DGGCs demonstrated significantly greater number of ACh-activated neurons per field than contralateral DGGCs (FIG. 4D). During 5 minutes of ACh perfusion, contralateral TBI had average of 2.6±0.2 events/neuron and ipsilateral TBI had 4.3±0.2 events/neuron (t(161)=4.90, p<0.0001), whereas sham control tissue averaged 1.8±0.3 events/neuron. The peak amplitude of $Ca^{2+}$ influx during ACh was 4.31±0.58 ΔF/F in ipsilateral TBI DGGCs, and 1.70±0.12 ΔF/F in contralateral DGGCs (t(209)=3.09, p=0.0025, FIG. 4E). Despite the increased variance in the peak amplitude of ipsilateral neurons, the duration of ipsilateral $Ca^{2+}$ influx (8.51±0.20 s) was consistently and significantly longer than in contralateral DGGCs (6.12±0.19 s) while remaining highly homoscedatic between the groups (t(209)=7.39, p<0.0001, FIG. 4F). These findings demonstrate that DGGCs exhibit emergent cholinergic sensitivity in response to TBI.

Figure 5A:
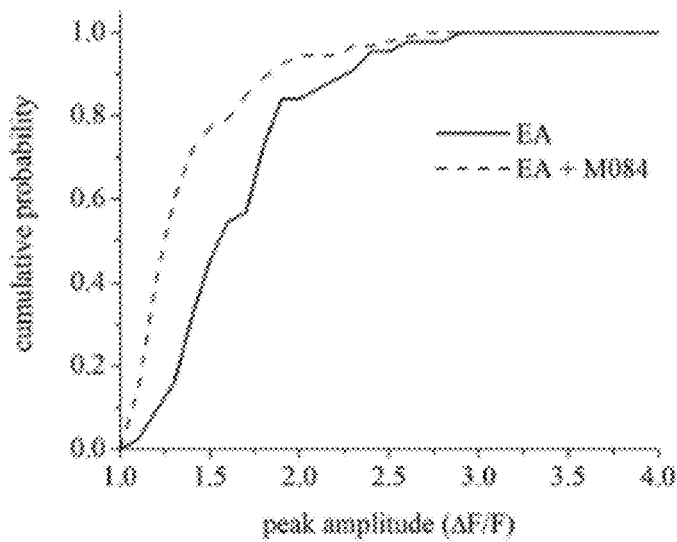
FIG. 5A-5D. TRPC4/5 channel antagonism blocks the prolonged $Ca^{2+}$ influx in DGGCs after CCI-TBI. Ipsilateral slice imaging of DGGC were subjected to the same baseline conditions as above in FIG. 4.
Figure 5B:
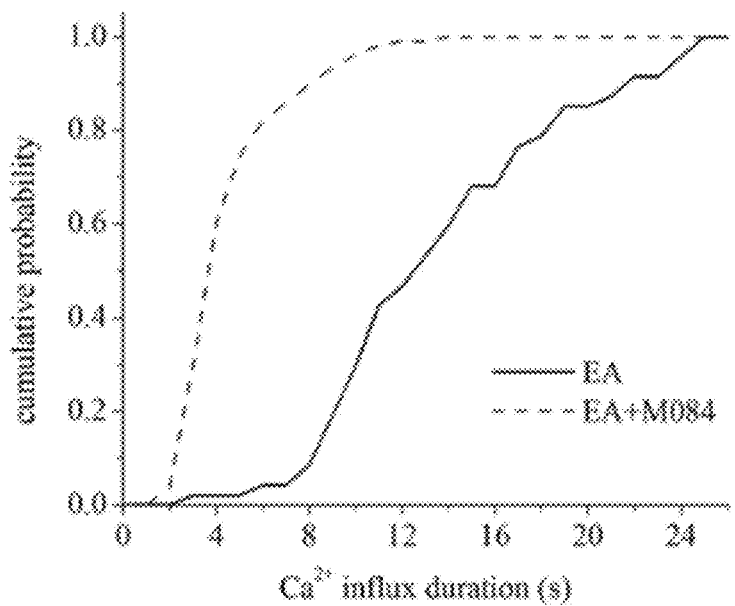
Figure 5C:
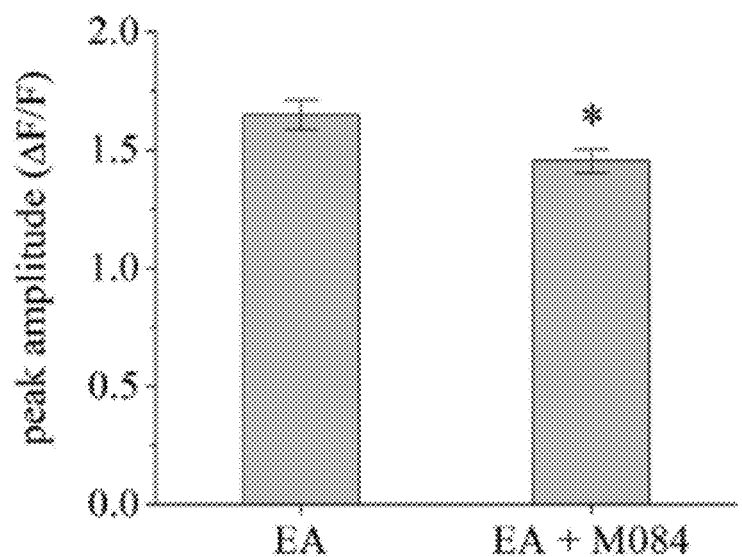
Figure 5D:
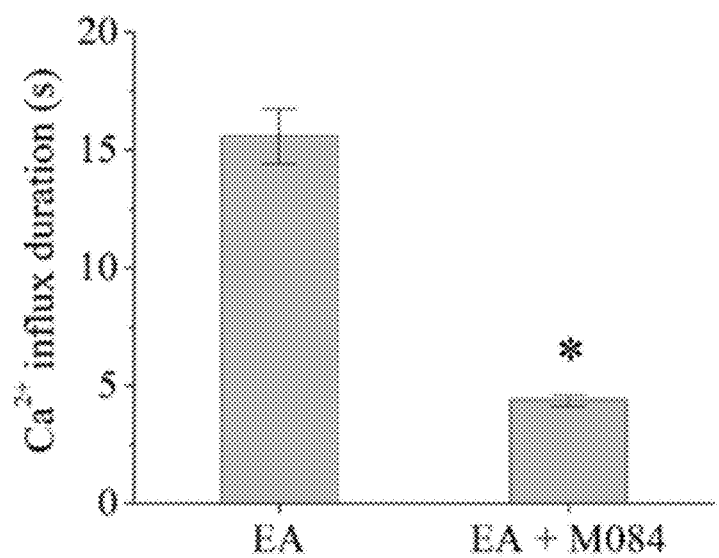

Englerin-A (EA) is a potent agonist of TRPC4/5 channels (Akbulut et al., 2015; Grant et al., 2019). We hypothesized that direct targeting of TRPC4-containing channels elicits robust, non-transient Ca2+ influx, similar to the cholinergic activity above. We measured Ca2+ activity in the absence and presence of a saturating concentration of EA (1 µM) in ipsilateral DGGCs from TBI mice. Compared to baseline conditions, Ca2+ peak amplitude from bath application of EA (1.66±0.06 ΔF/F) was not significantly altered from the baseline control condition (1.62±0.08 ΔF/F) (KS-test: D(74) =0.17, p=0.63). However, when M084 (10 µM) was added, the Ca2+ signal decreased significantly (1.44±0.05 ΔF/F; D(151)=0.42, p<0.001) (FIG. 5A, 5C). Interestingly, EA application alone resulted in considerably prolonged duration of Ca2+ entry into DGGCs with an average of 15.4±1.1 seconds (FIG. 5B, 5D). Addition of M084 attenuated the duration of influx to baseline levels, suggesting mediation of TRPC4/5-containing channels in this prolonged Ca2+ activity.

Figure 6A:
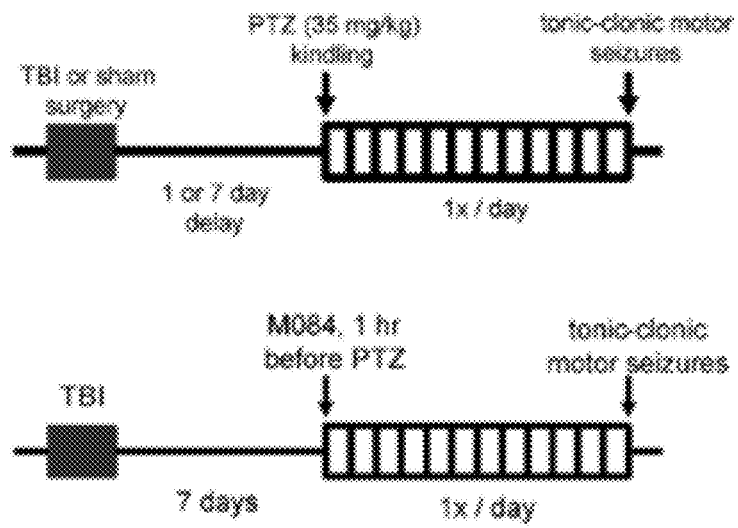
FIG. 6A-6G. Contribution of TRPC channels to post-trauma seizure susceptibility in mice.
Figure 6B:
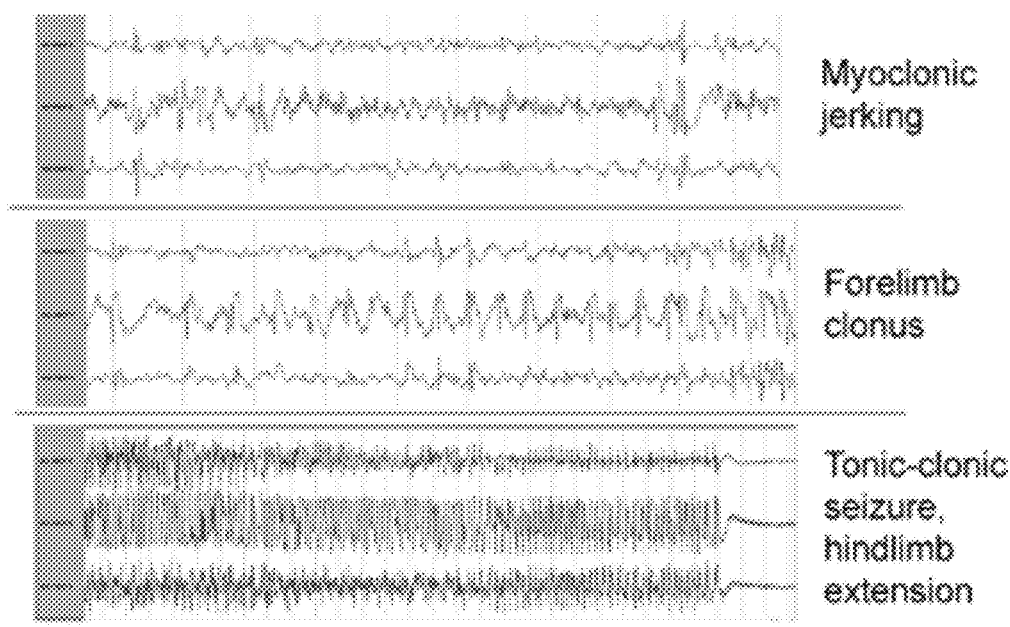
Figure 6C:
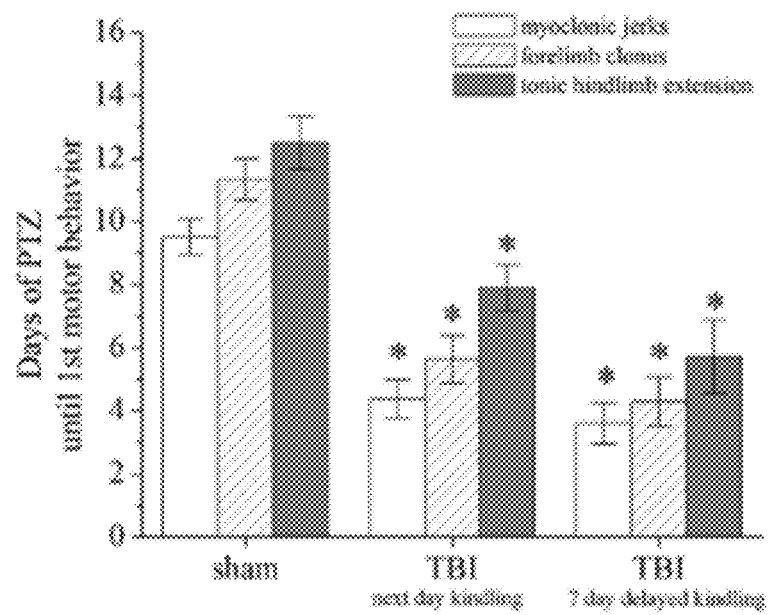
Figure 6D:
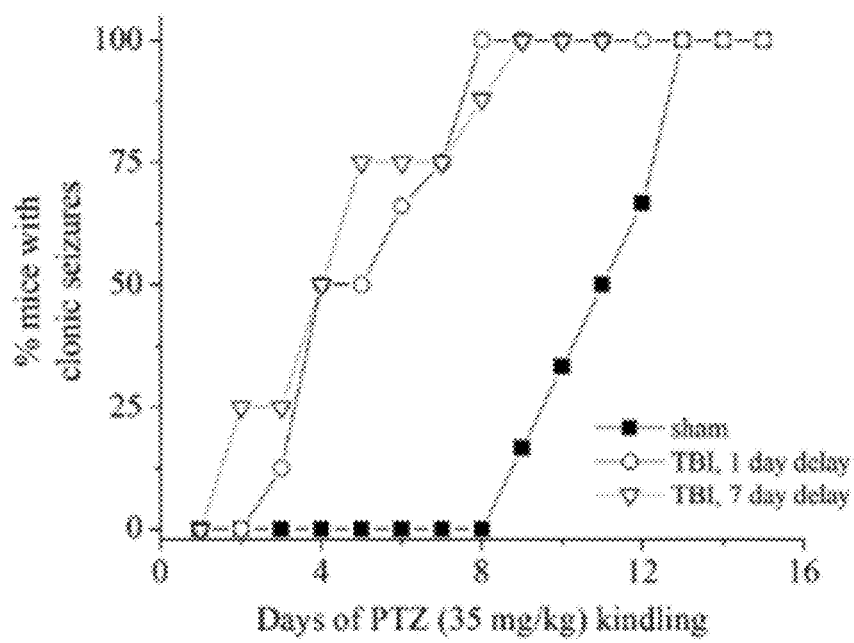

TBI facilitates TRPC-dependent seizure susceptibility. We have reported that in our model of CCI-TBI to adult mice, approximately one-third of animals exhibited epileptiform seizure activity six days after cortical impact, as measured by cortical EEG electrodes (Vigil et al., 2020). The fact that only a portion of TBI cases become susceptible to epileptic seizures is a yet unanswered phenomenon in both preclinical and clinical studies. Therefore, we investigated seizure susceptibility within the CCI-TBI model to gain a greater understanding as to the etiology of hyperexcitability spread occurring post-injury. CCI-TBI accelerates kindling epileptogenesis in rats, induced by the GABAA receptor antagonist pentylenetetrazol (PTZ) (Eslami et al., 2016). In addition, CCI-TBI results in greater seizure susceptibility to single-dose subconvulsant PTZ (Bolkvadze et al., 2016; Lu et al., 2020). In this study, we confirmed this by giving a single subconvulsant dose of 50 mg/kg PTZ at 7 days after TBI. The singular PTZ challenge resulted in 100% of mice acquiring myoclonic jerks (average latency to jerking: 7 min 16 sec±40 sec) and 86% of mice demonstrated forelimb clonus seizures (average latency to clonic seizure: 13 min 18 sec±2 min 5 sec) (n=14 mice). In our seizure susceptibility paradigm, 1 or 7 days after experimental procedure, mice were challenged with a subconvulsant dose of PTZ (35 mg/kg s.c.) once-daily to elicit kindling epileptogenesis (FIG. 6A). The progression of motor seizure behavior was observed and timed by direct observation linked to EEG activity (FIG. 6B). During the PTZ kindling that was initiated 1 day post-TBI (FIG. 6C), the average latencies to motor seizures in mice were: myoclonic jerks, (sham) 9.5±0.6 vs. (TBI) 4.4 ±0.6 days; forelimb clonus, (sham) 11.3±0.7 vs. (TBI) 5.6±0.7 days; and tonic-clonic seizure, (sham) 12.5±0.8 vs. (TBI) 7.9±0.7 days (p<0.001, Mann Whitney U test, n=6-8 per group). In the TBI group, five out of eight mice experienced lethal seizures on the second occurrence of tonic-clonic epileptic activity. It is important to note that these PTZ-induced seizures were induced in the presence of early pathophysiological changes in the brain such as inflammation and microgliosis 1-3 days after injury (Vigil et al., 2020). In mice with PTZ challenge initiated 7 days after TBI, the average latencies to seizure were: myoclonic jerks, (sham) 9.8±0.4 vs. (TBI) 3.6±0.7 days; forelimb clonus, (sham) 12.0±0.6 vs. (TBI) 4.3±0.8 days; and tonic-clonic seizure, (sham) 13.1±0.6 vs. (TBI) 5.6±1.2 days (FIG. 5C, p<0.01, Mann Whitney U test, n=6-7 per group). The progression of clonic activity was significantly escalated in the kindling mice initiated 1 day and 7 days after TBI (FIG. 6D). Therefore, TBI mice exhibited greater PTZ-induced seizure susceptibility overall in comparison to sham control mice.

TRPC4/5 antagonism reduces TBI-induced seizure susceptibility. TBI promotes a host of pathological alterations that include brain swelling, inflammation, cellular damage, neuronal death (Anderson et al., 2005), and increased neuron hyperexcitability which is key to the generation of epileptiform seizures (Santhakumar et al., 2001). We previously reported that antagonism of TRPC4/5-containing channels by M084 inhibited pilocarpine-induced seizure severity (Carver and Shapiro, 2019). A cohort of fully kindled mice were given M084 (10 mg/kg, s.c.) prior to PTZ-challenge (50 mg/kg) to test if TRPC4/5 blockade stifles seizure activity in non-muscarinic driven models of epilepsy. M084 administration prevented generalized seizure activity in 2 of 4 animals tested; seizure progression was destabilized and the mice were protected from clonic seizures, only displaying minimal jerking behavior. However, the other two animals challenged with PTZ experienced tonic-clonic seizures. All the control kindled mice that were given vehicle rather than M084 reached tonic-clonic episodes with tonic hindlimb extension. Therefore, the blockade of TRPC channel excitation may not fully suppress a reorganized epileptic network.

Figure 6E:
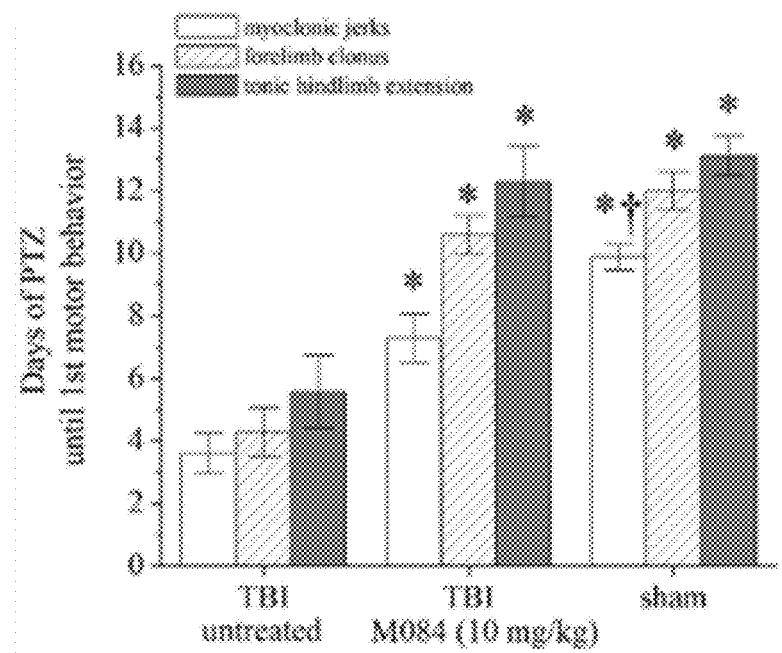
Figure 6F:
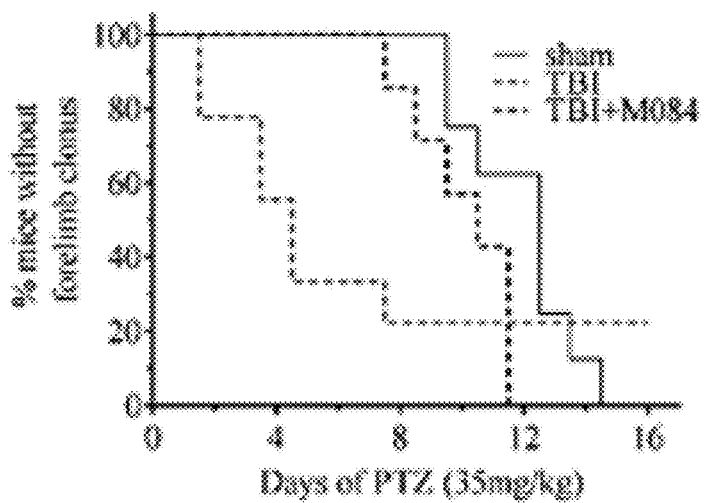
Figure 6G:
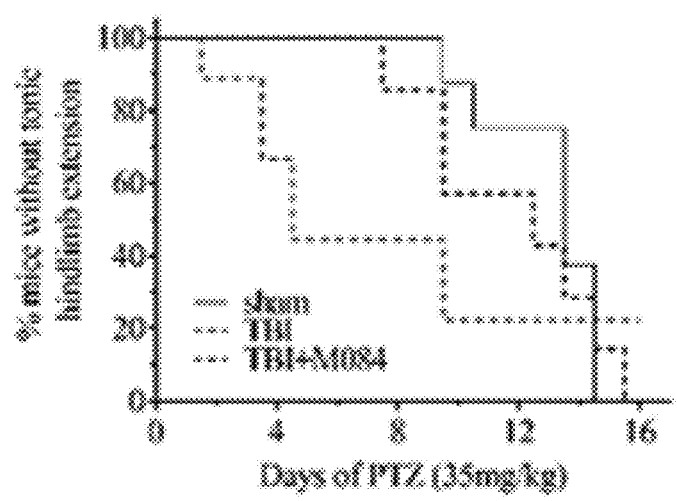

We wished to understand if the TRPC channel upregulation after TBI could be targeted to impede epileptogenic activity. Since we observed multi-region TRPC channel plasticity after TBI, we tested post-TBI seizure susceptibility in the presence of TRPC4/5 channel blockade. We tested a group of sham and TBI animals in which, 7 days after surgery, M084 (10 mg/kg, s.c.) was given 1 hour before each PTZ kindling challenge (35 mg/kg) (FIG. 6E). Therefore, at the time of PTZ challenge, brain concentration of M084 is likely within the micromolar range (Yang et al., 2015). Seizure susceptibility was standardized according to the latency to forelimb clonus lasting greater than 5 sec. We observed that TRPC4/5 antagonist impeded the rate of epileptogenesis (FIG. 6E-6G). M084 administration resulted in the mice requiring an average of 7.3±0.6 days to demonstrate myoclonic jerks, 10.6±0.5 days for clonic seizures, and 11.0±0.6 days to reach tonic-clonic seizure behavior. Thus, M084 treatment delayed the progression of seizures, displaying a greater latency than CCI-TBI mice without treatment, and similar to the rate of progression experienced by sham animals (FIG. 6E). The numbers of PTZ challenges required to reach forelimb clonus (FIG. 6F) and tonic hindlimb extension (FIG. 6G) seizure behaviors were prolonged significantly. These results suggest that TRPC4/5 channels may strongly contribute to seizure susceptibility after TBI, explored by an epileptogenic progression model. Previous TRPC knockout models ascertained susceptibility in response to pilocarpine, which acts directly on the muscarinic receptors (Phelan et al., 2012). Our novel approach determined seizure susceptibility in confirmation of acquired epileptogenesis after TBI, but these findings are consistent with a TRPC-specific role in contribution to neuronal hyperexcitability.

METHODS

Controlled cortical impact traumatic brain injury. The controlled cortical impact (CCI) traumatic brain injury (TBI) model was applied, with a closed skull impact approach. The CCI model causes TBI, but the skull remains intact with minimal hematoma. This type of brain injury model most closely simulates the TBI experienced during blunt-head injuries from vehicular accidents or falls. Mice were anesthetized with isoflurane (3% induction, 1% maintenance) in 100% $O_2$. Body temperature of 37° C. was maintained using a temperature-controlled heated surgical table. The skull was fixed with ear-bars into a stereotaxic frame. A small midline incision was made on the scalp using aseptic surgical techniques. Impact was delivered by cylindrical probe of 5 mm diameter with an Impact One neurotrauma impactor (Leica Biosystems). A calibrated impact was delivered at 4.5 m/sec to a depth of 1 mm and 0.5 sec dwell time to the right parietal cortex (−1.8 mm ML, +2.0 mm AP, −1.0 mm DV). Apnea episodes lasted between 10-60 sec after impact. The scalp was then sutured closed and mice were placed in a warming recirculation unit and monitored until fully awake and moving freely. Control littermate mice received anesthesia and sham surgery, but did not receive impact. For consistency, the left hemisphere of both sham and TBI mice is designated as "contralateral" brain, and the right hemisphere is referred to as "ipsilateral", despite no impact injury occurring in sham mice.

Western immunoblot of protein. Regional brain samples or microdissected brain slices were collected 2 hours, 2 days, or 7 days after sham surgery or TBI (ipsilateral and contralateral) and snap frozen in dry ice. Samples were homogenized on ice in a solution of RIPA buffer (Thermo Fisher), protease inhibitor tablet (Roche), and phosphatase inhibitor cocktail 2/3 (Sigma-Aldrich) using an Ultra EZgrind tissue homogenizer (Denville Scientific Inc.) at the lowest speed. Protein concentrations of each sample were determined using a Pierce BCA protein assay kit (Thermo Fisher). Protein samples (10-25 μg of total protein) were run in 10% precast polyacrylamide gels (Bio-rad) at 130 V for 1 h. Proteins were then transferred to PVDF membrane with a Transblot SD semi-dry transfer system (Bio-rad) at 15V for 15 min. Membranes were blocked with 5% BSA and stained with rabbit polyclonal antibodies for TRPC1 (1:1000, Alomone Labs #ACC-010, RRID:AB_2040234), TRPC4 (1:1000, Alomone Labs #ACC-018, RRID:2040239), TRPC5 (1:250, Sigma-Aldrich #T0325, RRID: AB_262146), or muscarinic acetylcholine receptor type 1 (1:2000, Millipore AB5164, RRID:AB_91713) for semi-quantification of proteins. Immunoblot bands were acquired via horseradish peroxidase-conjugated secondary antibodies and enhanced chemiluminescence western blotting detection reagents (GE Healthcare). Quantification of bands after exposure in the linear range used ImageJ software (National Institutes of Health). Proteins were normalized to mouse monoclonal β-actin antibody (1:20,000, Sigma-Aldrich #A5316 clone AC-74, RRID:AB_476743) at 42 kDa as a loading control. Results are standardized to the contralateral averages for each sham or TBI mice group.

Quantitative real-time PCR. Polymerase chain reaction studies were performed to quantify the mRNA levels of TRPC1/4/5 24hr and 7 days after CCI. Cortical and hippocampus samples were dissected and snap frozen in dry ice, and stored at −80° C. until analysis. Samples were homogenized in TRIzol buffer (Life) using an Ultra EZgrind tissue homogenizer (Denville Scientific) at the lowest speed. After chloroform extraction, total RNA was precipitated and resuspended in nuclease-free water. RNA quality and quantity were tested, for each sample, using a spectrophotometer (Nanodrop). cDNAs are synthetized with SuperScript III first-strand (Invitrogen) following manufacturer protocol. Oligo(dT)20 (Invitrogen) was used for mRNA specific amplification and 500 ng of total RNA used in each reaction. For amplification of TRPC1, TRPC4, TRPC5 and the housekeeping gene hypoxanthine phosphoribosyl transferase (HPRT) the primers were:

TRPC1:
F-ACCTTTGCCCTCAAAGTGGT, (SEQ ID NO: 1)
R-GCCCAAAATAGAGCTGGTTG; (SEQ ID NO: 2)

TRPC4:
F-GGAATCATGGGACATGTGG, (SEQ ID NO: 3)
R-CGGAGGGAACTGAAGATGTTT; (SEQ ID NO: 4)

TRPC5:
F-GTGGATTCACGGAATACATCC, (SEQ ID NO: 5)
R-TTGCCAGGTAGAGGGAGTTC; (SEQ ID NO: 6)

HPRT:
F-ATACAGGCCAGACTTTGTTGGATT, (SEQ ID NO: 7)
R-TCACTAATGACACAAACGTGATTCAA. (SEQ ID NO: 8)

qRT-PCR reactions are performed in a 7900 HT Fast Real-Time PCR system (Life Technologies) using SYBR Green PCR master mix (Thermo Fisher Scientific). The reaction begins with one-step of 95° C. for 10 minutes, followed by 40 cycles of 95° C. for 15 seconds and 60° C. for 1 minute. The number of cycles needed to reach exhaustion of the reaction, threshold cycle (CT) is determined. The difference between template CT and housekeeping gene CT (ΔCT) is calculated and transformed in power of 2 (2(−ΔΔCT)). Each sample is run in triplicates for each primer.

TRAP Neuronal Activity Assays. Targeted Recombination in Active Populations (TRAP) male mice were given 50 mg/kg 4-hydroxytamoxifen (4-OHT) to elicit cFos-labeling with td-Tomato (Guenther et al., 2013). 4-OHT was prepared by dissolution in 100% ethanol at a 10 mg/mL concentration. After evaporation of ethanol, sunflower seed oil was added to a final concentration of 5 mg/mL. 4-OHT was administered by i.p. injection either 12 hours prior to CCI-TBI or sham, or 7 days after CCI-TBI or sham. Another cohort of mice were given vehicle oil as a negative control, in which we detected no spontaneous td-Tomato fluorescence. At the conclusion of experiments, brain slices were acquired for stereology, as above. Brain slices were fixed and mounted with Vectashield containing DAPI to determine total percentage of neurons per field of view in imaging. 20× magnification images (561 nm emission filter cube) were acquired for each slice and hemisphere, with at least four separate slices for each region per brain. The number of td-Tomato+ parietal cortex layer 5 neurons and hippocampal principal neurons were quantified by a person who was blinded to the experimental group of the tissue. Individual mice each received an average count of td-Tomato+ neurons for each region. Then, single mouse counts were averaged from 5-6 mice per group.

Brain slice Ca2+ imaging. Transverse slices (300 μm) of hippocampus were cut with a vibratome (Thermo Scientific Microm HM650V) from Cre-CamK2+/GCamp6f+/− mice. Mice were anesthetized with isoflurane, and brains excised and placed in artificial cerebrospinal fluid (ACSF) at 3.5° C. composed of the following (in mM): 126 NaCl, 3 KCl, 0.5 $CaCl_2$, 0.5 $MgCl_2$, 26 $NaHCO_3$, 1.25 $NaH_2PO_4$, 15 glucose, 0.3 kynurenic acid, with pH adjusted to 7.35-7.40, with 95% $O_2$-5% $CO_2$, 305-315 mOsm/kg. Hippocampal slices were maintained in oxygenated ACSF at 30° C. for 60 min, and experiments performed at 28° C. Bath recording solution consisted of (in mM): 124 NaCl, 3 KCl, 1.5 MgCl$_2$, 2.4 CaCl$_2$, 1.25 Na$_2$H$_2$PO$_4$, 26 NaHCO$_3$, 15 glucose, 0.001 TTX, and 0.05 hexamethonium-Cl. Neurons were visually identified with a Nikon FN-1 microscope equipped with a 40× water-immersion objective and infrared differential interference contrast. GCaMP6f fluorescence was obtained using a SOLA Light Engine Illumination source (Lumecor) with an output of 3.5W through a 3 mm diameter liquid light guide through a Nikon ET-GFP filter. Nikon Elements software was used for image acquisition through a QIClick CCD camera (QImaging) with a Uniblitz Model VMM-D 1 shutter driver. Baseline time series of the DG granule layer were acquired in the presence of bath solution perfusion for 2 min. Experimentally, slices were then perfused with either Ach (0.3 mM), englerin A (1 µM EA), M084 (10 µM), La3+ (10 µM), or a combination thereof dissolved in bath solution at a flow rate of 2 mL/min for 5 min. Images were acquired in time series with an exposure time of 200 ms at 2-10 fps at 12-bit rate and no binning. Time-series image stacks were processed with ImageJ. Images were background subtracted using the mean of the 5% lowest pixel values. Ca2+ signal events were quantified for each cell as change in fluorescence divided by the baseline fluorescence (ΔF/F0) after background subtraction. ROI signals were detrended before quantification to account for drift due to gradual photobleaching of the background. Cellular events were thresholded by signal intensity greater than 1.5× the root mean square noise for the 2 min baseline recording. Group cell fluorescence data of active cells (Ca2+ influx) per field were averaged in comparison with cells from mice of sham control conditions.

In vivo electroencephalograms. To determine seizure frequency and record brain susceptibility to seizures, mice were implanted with electroencephalogram (EEG) electrodes 24 hr after sham or TBI. A three-channel tethered EEG system was used. The electrode pedestal (P1 Technologies) was secured to the skull with three anchored dental screws and connected to a preamplifier with gain of 25. The three leads were inserted over the left frontal cortex, left parietal cortex, and depth electrode lead into the hippocampus. The Stellate Harmonie acquisition hardware and software were used to collect coincident video and EEG activity. EEGs were inspected for presence of epileptiform spikes and seizures.

Seizure susceptibility assays. Pentylenetetrazol kindling model. Seizure susceptibility was tested with the GABAA receptor antagonist pentylenetetrazol (PTZ) for progression of motor seizure activity. Mice were injected with PTZ (35 mg/kg, s.c.) once per day and scored for motor behavioral seizures. Four stages of seizure response to PTZ were categorized: (1) a progressive decrease in activity and exploration until the animal came to rest in a crouched or prone position of hypoactivity, (2) myoclonic and jerking spasms characterized by brief focal seizures lasting 1 s or less, (c) generalized clonus characterized by sudden loss of upright posture, forelimb clonus, rearing, and autonomic signs, and (d) tonic-clonic seizure characterized by generalized seizure followed by tonic hindlimb extension. Latencies to focal (partial clonic), generalized (generalized clonic), and maximal (tonic-clonic) behavioral seizures were recorded and referenced by EEG recording of coincident electrical activity. Mice were monitored for 1 hr; however, they were considered without seizure if there was no incidence of forelimb clonus behavior within 30 min of injection. The initiation of daily PTZ administration began 24 hrs or 7 days after completion of sham or TBI surgery.

Experimental design and statistical analysis. Group data are displayed as the mean ± standard error of the mean (S.E.M.). All bar graphs depicted include individual data points Protein and mRNA expression samples were compared from group averages of ipsilateral vs. contralateral brain tissue. Each Ca2+ imaging experimental group was acquired from cells of at least 3-4 mice. Assessment of group data expected to be normally distributed was completed by the Kolmogorov-Smirnov test using the sham control data in relation to the empirical distribution function. Statistical comparisons of parametric measures, including electrophysiology data, were performed using an independent, two-tailed t test, followed by Tukey's HSD test post hoc. Non-parametric data were analyzed with a Mann-Whitney U test for independent samples, and the Wilcoxin signed-rank test was applied for dependent samples. The criterion for statistical significance was p<0.05 unless otherwise specified.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

1. Akbulut et al. (2015) Angew Chem Int Ed Engl 54:3787-3791.
2. Alexander et al. (2009) Neuron 63:27-39.
3. Baker et al. (2013) Neurosci Biobehav Rev 37:1211-1239.
4. Bal et al. (2010) J Neurosci 30:2311-2323.
5. Balla et al. (2008) Mol Biol Cell 19:711-721.
6. Battefeld et al. (2014) J Neurosci 34:3719-3732.
7. Becker et al. (2008) J Neurosci 28:13341-13353.
8. Beech et al. (1991) Proc Natl Acad Sci U S A 88:652-656.
9. Bergson et al. (2011) Mol Pharmacol 79:411-419.
10. Bernheim et al. (1991) Neuron 6:859-867.
11. Biervert et al. (1998) Science 279:403-406.
12. Boulay et al. (1999) Proc Natl Acad Sci USA 96:14955-14960.
13. Broker-Lai et al. (2017) EMBO J 36:2770-2789.
14. Brown and Adams (1980) Nature 283:673-676.
15. Brown and Passmore (2009) Br J Pharmacol 156:1185-1195.
16. Brown et al. (2008) Biophys J 95:1795-1812.
17. Bymaster et al. (2003) Eur J Neurosci 17:1403-1410.
18. Carver et al. (2014) J Neurosci 34:14181-14197.
19. Chiang et al. (2010) Neuroscience 169:39-51.
20. Christensen et al. (2009) Lancet 373:1105-1110.
21. Chung et al. (2006a) Proc Natl Acad Sci U S A 103:8870-8875.
22. Chung et al. (2006b) Brain Res 1085:132-137.
23. Cohen et al. (2007) Prog Brain Res 161:143-169.
24. Constanti and Brown (1981) Neurosci Lett 24:289-294.
25. Cooper and Jan (2003) Arch Neurol 60:496-500.
26. Cooper et al. (2001) J Neurosci 21:9529-9540.
27. Coulter and Carlson (2007) Prog Brain Res 163:235-243.
28. Cui and Strowbridge (2018) J Neurosci 38:423-440.
29. Delmas and Brown (2002) Neuron 36:787-790.
30. Dengler et al. (2017) Sci Rep 7:42090.
31. de Rubio et al. (2018) Sci Signal 11:eaan1210.
32. Di Paolo et al. (2004) Nature 431:415-422.
33. Falkenburger et al. (2010) J Gen Physiol 135:99-114.
34. Fano et al. (2012) Eur J Neurosci 36:3628-3635.

35. Fidzinski et al. (2015) Nat Commun 6:6254.
36. Finch and Augustine (1998) Nature 396:753-756.
37. Fiszman et al. (1991) Brain Res 557:1-4.
38. Fowler et al. (2007) PLoS One 2:e573.
39. Frey (2003) Epilepsia 44(Suppl 10): 11-17.
40. Gafni et al. (1997) Neuron 19:723-733.
41. Gamper and Shapiro(2015) KCNQ channels. In: Handbook of ion channels, Ed 1 (Zheng J, Trudeau MC, eds), pp 275-306. Boca Raton, FL: CRC. Google
42. Gamper et al. (2003) J Neurosci 23:84-95.
43. Gamper et al. (2004) J Neurosci 24:1098D-10992.
44. Garga and Lowenstein (2006) Epilepsy Curr 6:1-5.
45. Gessner and Heincmann (2003) BrJ Pharmacol 138:161-171.
46. Glaaser and Slesinger (2017) Sci Rep 7:4592.
47. Golarai et al. (1992) Brain Res 593:257-264.
48. Greene and Hoshi (2017) Cell Mol Life Sci 74:495-508.
49. Gu et al. (2005) J Physiol 566:689-715.
50. Gunthorpe et al. (2012) Epilepsia 53(3):412-424.
51. Gustina and Trudeau (2009) Proc Natl Acad Sci U S A 106:13082-13087.
52. Hadley et al. (2000) Br J Pharamacol 129:413-415.
53. Hamilton et al. (1997) Proc Natl Acad Sci USA 94:13311-13316.
54. He et al. (2012) J Neurosci 32:9383-9395.
55. Henze et al. (2002) Nature Neurosci 5(8):790-795.
56. Hernandez et al. (2008a) J Gen Physiol 132:361-381.
57. Hernandez et al. (2008b) J Physiol 586:1811-1821.
58. Hernandez et al. (2009) J Gen Physiol 134:437-448.
59. Hester and Danzer (2013) J Neurosci 33:8926-8936.
60. Hilgemann (2007) Pflugers Arch 455:55-67.
61. Holmes GL, Sarkisian M, Ben-Ari Y, Chevassus-Au-Louis N (1999) Mossy fiber sprouting after recurrent seizures during early development in rats. J Comp Neurol 404:537-553.
62. Homayoun et al. (2000) Neurochem Res25:269-275.
63. Horowitz et al. (2005) J Gen Physiol 126:243-262.
64. Hoshi et al. (2003) Nat Neurosci 6:564-571
65. Hoshi et al. (2005) Nat Cell Biol 7:1066-1073.
66. Hu et al. (2002) J Physiol 545:783-805.
67. Hu et al. (2007) J Neurosci 27:1853-1867.
68. Huang et al. (1998) Nature 391:803-806.
69. Hunt et al. (2009) Exp Neurol 215:243-252.
70. Itou et al. (2011) Hippocampus 21:446-459.
71. Jan and Jan (2012) J Physiol 590:2591-2599.
72. Jiang et al. (1994) Brain Res 651:123-128.
73. Jung and McNaughton (1993) Hippocampus 3:165-182.
74. Karschin et al. (1996) J Neurosci 16:3559-3570.
75. Kim et al. (2016a) eLife 5:e17159.
76. Kim et al. (2016b) Biophys J 110:1089-1098.
77. Klinger et al. (2011) Neuroimage 58:761-769.
78. Ko and Kang (2017) Neuropharmacology 121:120-129.
79. Kobayashi and Buckmaster (2003) J Neurosci 23:2440-2452.
80. Kochanek ett al. (2006) J Cereb Blood Flow Metab 26:565-575.
81. Kosenko and Hoshi (2013) PLOS One 8:e82290.
82. Kosenko et al. (2012) EMBO J 31 3147-3156.
83. Krook-Magnuson et al. (2015) J Physiol 593:2379-2388.
84. Langmead et al. (2008) Br J Pharmacol 154:1104-1115.
85. Larsen (2010) Pflugers Arch 460:803-812.
86. Lassing and Lindberg (1990) FEBS Lett 262:231-233.
87. Lawrence et al. (2006a) J Physiol 571:555-562.
88. Lawrence et al. (2006b) J Neurosci 26:12325-12338.
89. Lawrence et al. (2006c) J Physiol 570:595-610.
90. Leão et al. (2009) J Neurosci 29:13353-13364.
91. Levey et al. (1995) J Neurosci 15:4077-4092.
92. Li et al. (2004) J Biol Chem 279:45399-45407.
93. Li et al. (2005) J Neurosci 25:9825-9835.
94. Loew (2007) J Physiol 582:945-951.
95. Logothetis et al. (2015) Int Rev Neurobiol 123:1-26.
96. Lowenstein (2009) Epilepsia 50(Suppl 2):4-9.
97. Lübke et al. (1998) J Neurophysiol 79:1518-1534.
98. Lüscher and Slesinger (2010) Nat Rev Neurosci 11:301-315.
99. Lüscher et al. (1997) Neuron 19:687-695.
100. Lyeth et al. (1996) Brain Res 742:63-70.
101. Madison et al. (1987) J Neurosci 7:733-741.
102. Madroñal et al. (2016) Nat Commun 7:10923.
103. Martinello et al. (2015) Neuron 85:346-363.
104. Mateos-Aparicio et al. (2014) J Physiol 592:669-693.
105. McHugh et al. (2007) Science 317:94-99.
106. Michel et al. (2005) Neuropharmacology 48:796-809.
107. Miller et al. (2011) J Biol Chem 286:33436-33446.
108. Mori et al. (2015) Front Pharmacol 6:22.
109. Mucha et al. (2010) J Neurosci 30:13235-13245.
110. Nicoll (2017) Neuron 93:281-290.
111. Niday et al. (2017) J Neurosci 37:576-586.
112. Nilsson et al. (1994) Brain Res 637:227-232.
113. Nyakas et al. (1987) Brain Res Bull 18:533-545.
114. Ordaz et al. (2005) J Biol Chem 280:30788-30796.
115. Otto et al. (2002) Mol Pharmacol 61:921-927.
116. Owsianik et al. (2006) Annu Rev Physiol 68:685-717.
117. Pan et al. (2006) J Neurosci 26:2599-2613.
118. Papke et al. (2010) J Pharmacol Exp Ther 333:501-518.
119. Peters et al. (2005) Nat Neurosci 8:51-60.
120. Petrovic et al. (2012) PLoS One 7:e30402.
121. Phelan et al. (2012) Mol Pharmacol 81:384-392.
122. Phelan et al. (2017) Epilepsia 58:247-254.
123. Ponce et al. (1996) J Neurosci 16:1990-2001.
124. Poolos and Johnston (2012) Epilepsia 9:32-40.
125. Pottker et al. (2017) Brain Struct Funct 222:4005-4021.
126. Prakriya and Lewis (2015) Physiol Rev 95:1383-1436.
127. Racaud-Sultan et al. (1993) FEBS Lett 330:347-351.
128. Racine (1972) Electroencephalogr Clin Neurophysiol 32:281-294.
129. Ramsey et al. (2006) Annu Rev Physiol 68:619-647.
130. Reddy and Kuruba (2013) Int J Mol Sci 14:18284-18318.
131. Ren et al. (2013). J Cereb Blood Flow Metab 33: 834-845.
132. Robbins et al. (2013) PLoS One 8:e71809.
133. Roth (2016) Neuron 89:683-694.
134. Rouse et al. (2000) Neurosci Lett 278:61-64.
135. Rubaiy et al. (2017) J Biol Chem 292:8158-8173.
136. Rundfeldt and Netzer (2000) Neurosci Lett 282:73-76.
137. Saganich et al. (2001) J Neurosci 21:4609-4624.
138. Santhakumar et al. (2005) J Neurophysiol 93:437-453.
139. Scharfman and Myers (2016) Neurobiol Learn Mem 129:69-82.
140. Schroeder et al. (1998) Nature 396:687-690.
141. Schroeder et al. (2000) J Biol Chem 275:24089-24095.
142. Selyanko et al. (2001) J Physiol 534:15-24.
143. Shah et al. (2008) Proc Natl Acad Sci U S A 105:7869-7874.
144. Shapiro et al. (2000) J Neurosci 20:1710-1721.
145. Sheffler et al. (2009) Mol Pharmacol 76:356-368.
146. Shen et al. (2005) J Neurosci 25:7449-7458.
147. Singh et al. (1998) Nat Genet 18:25-29.
148. Singh et al. (2008) J Physiol 586:3405-3423.
149. Slesinger et al. (1997) Proc Natl Acad Sci U S A 94:12210-12217.
150. Sloviter et al. (2012) Abnormal dentate gyrus network circuitry in temporal lobe epilepsy. In: Jasper's basic mechanisms of the epilepsies, Ed 4 (Noebels J L, Avoli M, Rogawski M A, Olsen R W, Delgado-Escueta A V eds). Bethesda: National Center for Biotechnology Information. Google
151. Smith et al. (2012) J Vis Exp 69:4411
152. Smith et al. (2015) J Neurotrauma 32(22): 1725-1735.
153. Soh et al. (2014) J Neurosci 34:5311-5321.
154. Sohn et al. (2007) J Physiol 582:1037-1046.
155. Sotty et al. (2003) J Physiol 551:927-943.
156. Storch et al. (2012) J Biol Chem 287:3530-3540.
157. Strübing et al. (2001) Neuron 29:645-655.
158. Suh and Hille (2007) J Physiol 582:911-916.
159. Suh et al. (2004) J Gen Physiol 123:663-683.
160. Tai et al. (2011) Hippocampus 21:958-967.
161. Takano and Coulter (2012) In: Jasper's basic mechanisms of the epilepsies, Ed 4 (Noebels J L, Avoli M, Rogawski M A, Olsen R W, Delgado-Escueta A V eds). Bethesda: National Center for Biotechnology Information. Google
162. Takechi et al. (1998) Nature 396:757-760.
163. Talley Watts et al. (2013) J Neurotrauma 30: 55-66.
164. Tatulian and Brown (2003) J Physiol 549:57-63.
165. Tatulian et al. (2001) J Neurosci 21:5535-5545.
166. Telezhkin et al. (2012) J Gen Physiol 140:41-53.
167. Thomas et al. (2008) J Pharmacol Exp Ther 327:365-374.
168. Trebak et al. (2009) Pflugers Arch 457:757-769.
169. Tuosto et al. (2015) Cell Mol Life Sci 72:4461-4474.
170. Tzingounis and Nicoll (2008) Proc Natl Acad Sci U S A 105:19974-19979.
171. Tzingounis et al. (2010) Proc Natl Acad Sci U S A 107:10232-10237.
172. Vagnerova et al. (2009) Anesth Analg 1 C7:201-214.
173. Venkatachalam et al. (2003) J Biol Chem 278:29031-29040.
174. Vervaeke et al. (2006) J Physiol 576:235-256.
175. Vogt and Regehr (2001) J Neurosci 21:75-83.
176. Volpicelli and Levey (2004) Prog Brain Res 145:59-66.
177. Volpicelli-Daley et al. (2010) J Biol Chem 285:28708-28714.
178. Wang et al. (1998) J Gen Physiol 112:637-647.
179. Watanabe et al. (1996) J Neurosci 16:3827-3836.
180. Winks et al. (2005) J Neurosci 25:3400-3413.
181. Wright et al. (2014) Neuron 82:836-847.
182. Wu et al. (2010) Pharm Rev 62:381-404.
183. Wu et al. (2008) J Neurophysiol 100:1897-1908.
184. Xu and Loew (2003) Biophys J 84:4144-4156.
185. Xu et al. (2003) J Cell Biol 161:779-791.
186. Xu et al. (2017) Sci Immunol 2:eaan0787.
187. Yang et al. (2015) PLoS One 10:e0136255.
188. Yue and Yaari (2004) J Neurosci 24:4614-4624.
189. Yue and Yaari (2006) J Neurophysiol 95: 3480-3495.
190. Zaczek et al. (1998) J Pharmacol Exp Ther 285:724-730.
191. Zaika et al. (2007) J Neurosci 27:8914-8926.
192. Zaika et al. (2008) Biophys J 95:5121-5137.
193. Zaika et al. (2011) J Biol Chem 286:830-841.
194. Zeng et al. (2015) Mol Neurobiol 52:562-572.
195. Zhang et al. (2003) Neuron 37:963-975.
196. Zhang et al. (2016) Neuron 92:461-478.
197. Zhang and Shapiro (2012) Neuron 76:1133-1146.
198. Zhang et al. (2011) J Neurosci 31:7199-7211.
199. Zheng (2017) Adv Exp Med Biol 976:123-135.
200. Zheng and Phelan (2014) Cells 3:288-303.
201. Zhou et al. (2013) Proc Natl Acad Sci U S A 110:8726-8731.
202. Zhou and Neher(1993) J Physiol 469:245-273.
203. Zhu et al. (2016) Genesis 54:439-446.
204. Zhu et al. (2015) Br J Pharmacol 172:3495-3509.
205. Zimmerman et al. (2008) Eur J Neurosci 27:965-975.

The invention claimed is:

1. A method of treating a subject that has experienced a traumatic brain injury (TBI) comprising administering to the subject having experienced a_TBI a selective small molecule inhibitor of Transient Receptor Potential-Canonical (TRPC) 4/5 channel.

2. The method of claim 1, wherein the selective small molecule inhibitor of TRPC4/5 channel is M084 hydrochloride.

3. The method of claim 1, wherein the selective small molecule inhibitor of TRPC4/5 channel is ML204.

4. The method of claim 1, wherein the selective small molecule inhibitor of TRPC4/5 channel is administered to the subject by a route selected from among a parenteral, intravenous, intraarterial, intramuscular, intracranial, intraorbital, nasal, or intraventricular route.

5. The method of claim 1, further comprising administering one or more additional therapeutic agents to the subject.

6. The method of claim 5, wherein the one or more additional therapeutic agent is selected from among a neuroprotective agent, an anticonvulsant agent, an antiepileptic agent, or a combination thereof.

7. The method of claim 5, wherein the selective small molecule inhibitor of TRPC4/5 channel is administered to the subject before, at the same time, or after the additional therapeutic agent is administered to the subject.

8. The method of claim 1, wherein the subject is a human subject.

9. A method of treating a subject that has experienced a traumatic brain injury (TBI) comprising administering to a subject having experienced a TBI a selective small molecule inhibitor of Transient Receptor Potential-Canonical (TRPC) 4/5 channel selected from M084 and ML204.

* * * * *

```
                        SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
acctttgccc tcaaagtggt                                                    20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
gcccaaaata gagctggttg                                                    20

<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide
```

```
<400> SEQUENCE: 3
ggaatcatgg gacatgtgg                                              19

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
cggagggaac tgaagatgtt t                                           21

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
gtggattcac ggaatacatc c                                           21

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
ttgccaggta gagggagttc                                             20

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 7
atacaggcca gactttgttg gatt                                        24

<210> SEQ ID NO 8
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 8
tcactaatga cacaaacgtg attcaa                                      26
```